United States Patent
Tokunaga

(10) Patent No.: US 9,869,685 B2
(45) Date of Patent: Jan. 16, 2018

(54) SAMPLE ANALYZER

(75) Inventor: Kazutoshi Tokunaga, Kakogawa (JP)

(73) Assignee: Sysmex Corporation, Kobe-shi, Hyogo (JP)

( * ) Notice: Subject to any disclaimer, the term of this patent is extended or adjusted under 35 U.S.C. 154(b) by 299 days.

(21) Appl. No.: 13/051,445

(22) Filed: Mar. 18, 2011

(65) Prior Publication Data

US 2011/0229374 A1     Sep. 22, 2011

(30) Foreign Application Priority Data

Mar. 18, 2010   (JP) ................ 2010-062097
Mar. 24, 2010   (JP) ................ 2010-068422

(51) Int. Cl.
G01N 35/02    (2006.01)
G01N 35/04    (2006.01)
G01N 35/00    (2006.01)

(52) U.S. Cl.
CPC ....... *G01N 35/04* (2013.01); *G01N 35/00732* (2013.01); *G01N 2035/00742* (2013.01); *G01N 2035/00782* (2013.01); *G01N 2035/0443* (2013.01)

(58) Field of Classification Search
None
See application file for complete search history.

(56) References Cited

U.S. PATENT DOCUMENTS

| | | | |
|---|---|---|---|
| 5,500,651 A * | 3/1996 | Schuermann | 342/42 |
| 2004/0258565 A1* | 12/2004 | Watari | 422/64 |
| 2009/0134978 A1* | 5/2009 | Imai | 340/10.6 |

FOREIGN PATENT DOCUMENTS

| | | |
|---|---|---|
| JP | 10-107726 | 4/1998 |
| JP | 2007-081825 | 3/2007 |
| JP | 2008-020335 | 1/2008 |
| JP | 2008-140020 | 6/2008 |
| JP | 2008-261753 | 10/2008 |
| JP | 2009-053851 | 3/2009 |
| JP | 2009-210444 A | 9/2009 |

OTHER PUBLICATIONS

Jun-Bong Eom et al: "An Efficient Reader Anticollision Algorithm in Dense RFID Networks With Mobile RFID Readers", IEEE Transactions on Industrial Electronics, IEEE Service Center, Piscataway, NJ, USA, vol. 56, No. 7, Jul. 1, 2009 (Jul. 1, 2009), pp. 2326-2336, XP011257425, ISSN: 0278-0046.

* cited by examiner

*Primary Examiner* — P. Kathryn Wright
(74) *Attorney, Agent, or Firm* — Sughrue Mion, PLLC

(57) ABSTRACT

A sample analyzer including: a first reagent container holding unit; a second reagent container holding unit being arranged on one side of the first reagent container holding portion; a reagent information reading unit; and a control unit. The reagent information reading unit includes an electric wave emitting portion, which is arranged on the other side of the first reagent container holding unit, for emitting a plurality of electric waves having mutually differing reaching ranges, and the control unit controls the reagent information reading unit to switch the electric wave emitted from the electric wave emitting portion in accordance with a read target being the first electronic tag or the second electronic tag.

15 Claims, 22 Drawing Sheets

SAMPLE ANALYZER

FIELD OF THE INVENTION

The present invention relates to a sample analyzer, and in particular, to a sample analyzer for mounting a reagent container with an electronic tag recorded with reagent information.

BACKGROUND

A sample analyzer for mounting a reagent container with an electronic tag recorded with reagent information is conventionally known.

Japanese Patent Publication No. 2009-210444 discloses an automatic analyzer including: a circular ring-shaped reagent container holding unit for holding a plurality of reagent containers with a wireless IC tag recorded with reagent information in two rows of an inner peripheral row and an outer peripheral row; an inner peripheral antenna for emitting an electric wave to the wireless IC tag of the reagent container held at the reagent container holding unit of the inner peripheral row; an outer peripheral antenna for emitting an electric wave to the wireless IC tag of the reagent container held at the reagent container holding unit of the outer peripheral row; and an information reading and recording portion for receiving the electric wave returned from the wireless IC from the inner peripheral antenna and the outer peripheral antenna. In the automatic analyzer, the inner peripheral antenna is arranged on the inner side of the reagent container holding unit of the inner peripheral row, and the outer peripheral antenna is arranged on the outer side of the reagent container holding unit of the outer peripheral row.

However, in the automatic analyzer described in Japanese Patent Publication No. 2009-210444, the region on the inner side of the reagent container holding unit of the inner circumferential row and the region on the outer side of the reagent container holding unit of the outer peripheral row need to be ensued to arrange the antenna, which enlarges the apparatus.

SUMMARY

The scope of the present invention is defined solely by the appended claims, and is not affected to any degree by the statements within this summary.

A first aspect of the present invention is a sample analyzer for analyzing a sample using a reagent in a reagent container comprising: a first reagent container holding unit configured to hold a first reagent container attached with a first electronic tag recorded with reagent information regarding a reagent; a second reagent container holding unit configured to hold a second reagent container attached with a second electronic tag recorded with reagent information regarding a reagent, and being arranged on one side of the first reagent container holding unit; a reagent information reading unit comprising an electric wave emitting portion and configured to read the reagent information recorded in the first electronic tag and the reagent information recorded in the second electronic tag; and a control unit for the reagent information reading unit, wherein the electric wave emitting portion is arranged on a side other than the one side of the first reagent container holding unit and is configured to emit a plurality of electric waves having mutually differing reaching ranges, and wherein the control unit controls the reagent information reading unit to switch the electric wave emitted from the electric wave emitting portion in accordance with a read target being the first electronic tag or the second electronic tag.

A second aspect of the present invention is a sample analyzer for analyzing a sample using a reagent in a reagent container comprising: a first reagent container holding unit configured to hold a first reagent container attached with a first electronic tag recorded with reagent information regarding a reagent; a second reagent container holding unit configured to hold a second reagent container attached with a second electronic tag recorded with reagent information regarding a reagent, and being arranged on one side with respect to the first reagent container holding unit; an antenna, arranged on a side other than the one side with respect to the first reagent container holding unit and is configured to receive respective electric waves from the first electronic tag of the first reagent container and from the second electronic tag of the second reagent container; and a reagent information acquiring unit configured to acquire the reagent information recorded in the first electronic tag based on the electric wave received by the antenna from the first electronic tag, and to acquire the reagent information recorded in the second electronic tag based on the electric wave received by the antenna from the second electronic tag.

DETAILED DESCRIPTION OF THE EMBODIMENT

The embodiments embodying the present invention will be described below based on the drawings.
(First Embodiment)

The configuration of an immune analyzer 1 according to a first embodiment of the present invention will be described first with reference to FIGS. 1 to 17.

The immune analyzer 1 according to the first embodiment of the present invention is an apparatus for carrying out examinations on various items such as protein related to infectious disease (hepatitis B, hepatitis C, etc.), tumor marker, and thyroid hormone by using sample such as blood.

The immune analyzer 1 is an apparatus for performing quantitative measurement or qualitative measurement on antigen, antibody, and the like contained in the sample (blood specimen) such as blood, which is the measurement target. When quantitatively measuring the antigen contained in the sample, the immune analyzer 1 bonds magnetic particles (R2 reagent: second reagent) to a capture antibody (R1 reagent: first reagent) bonded to an antigen contained in the sample, and thereafter, attracts the bound antigen, capture antibody, and magnetic particles to a magnet (not shown) of a primary BF (Bound Free) separator 11 to remove the R1 reagent containing non-reactive (free) capture body. The immune analyzer 1 then bonds the antigen bound with magnetic particles and a labeled antibody (R3 reagent), and thereafter, attracts the bound magnetic particles, antigen, and labeled antibody to a magnet (not shown) of a secondary BF separator 12 to remove the R3 reagent containing non-reactive (free) labeled antibody. Furthermore, a dispersion liquid (R4 reagent) and a light emission substrate (R5 reagent) that emits light in the reaction process with the labeled antibody are added, and the light emission amount generated by the reaction of the labeled antibody and the light emission substrate is measured. The antigen contained in the sample that bonds with the labeled antibody is quantitatively measured through such processes.

Figure 1:
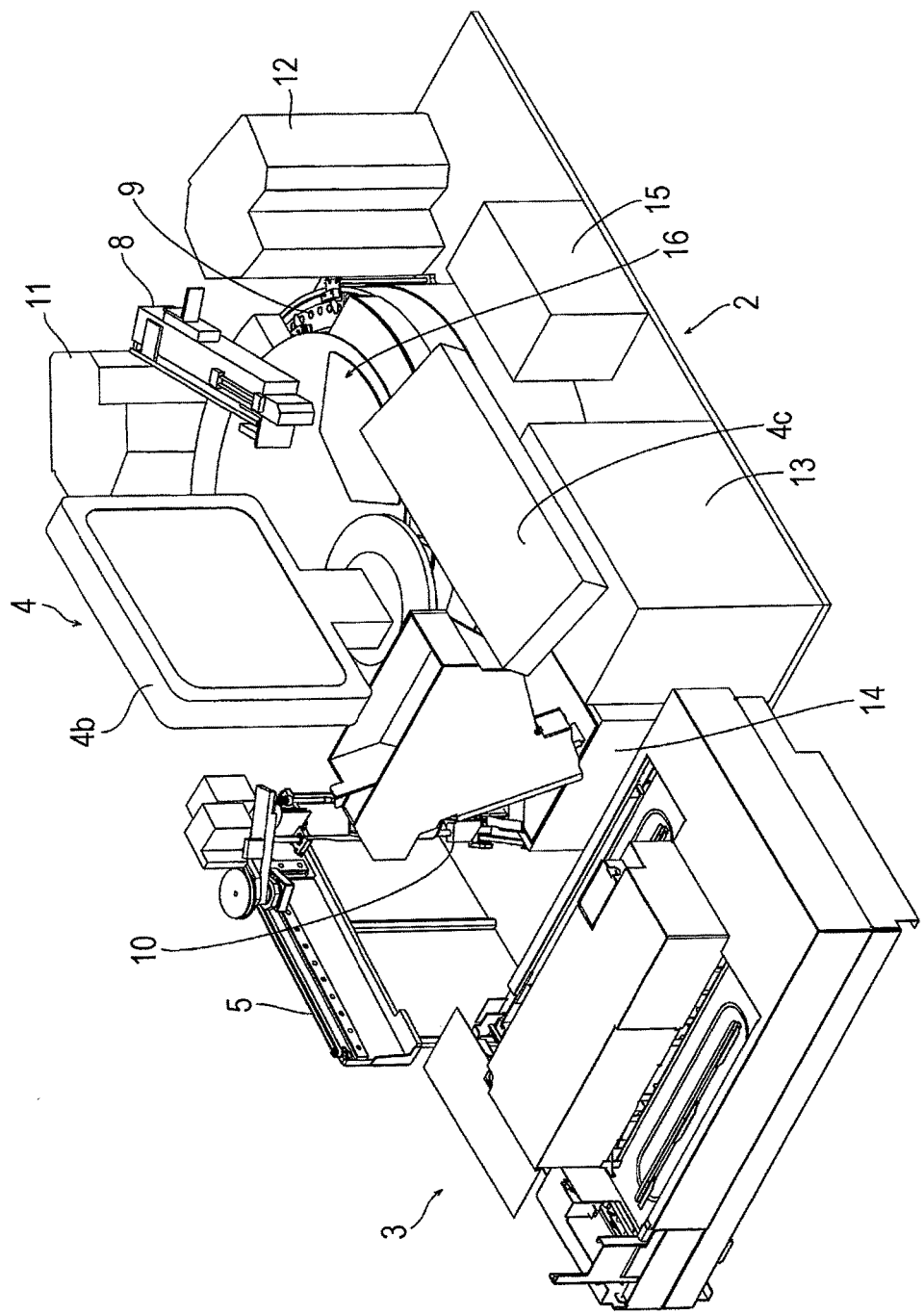
FIG. 1 is a perspective view showing an overall configuration of an immune analyzer according to a first embodiment of the present invention.
Figure 2:
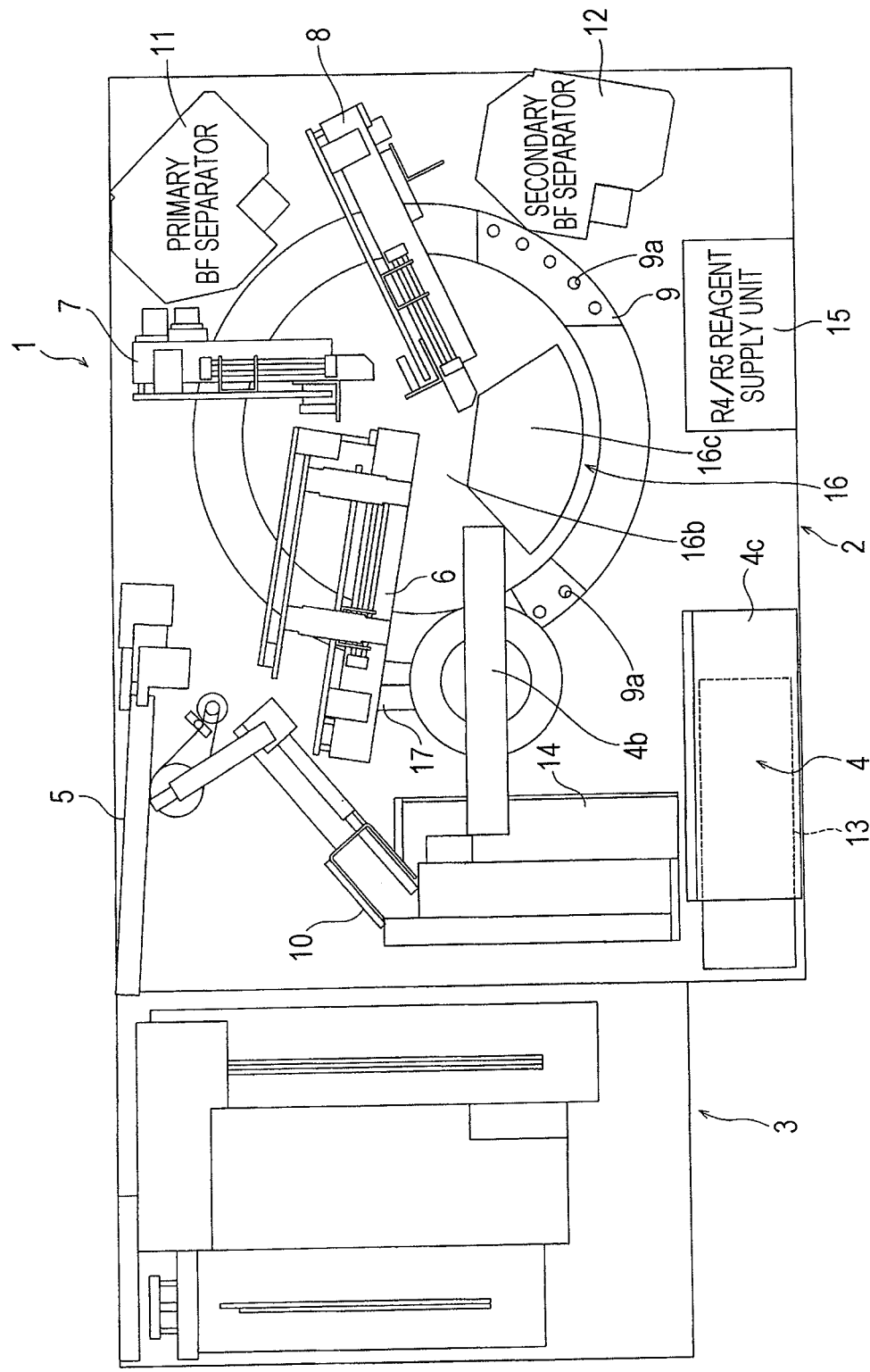
FIG. 2 is a plan view showing an overall configuration of the immune analyzer according to the first embodiment shown in FIG. 1.

As shown in FIGS. 1 and 2, the immune analyzer 1 includes a measurement mechanism section 2, a sample transport section (sampler) 3 arranged adjacent to the measurement mechanism section 2, and a control device 4 including PC (personal computer) electrically connected to the measurement mechanism section 2.

The sample transport section 3 is configured to transport a rack mounted with a plurality of test tubes (not shown) accommodating samples. The sample transport section 3 is configured to transport the test tube accommodating the sample to a sample aspirating position by a sample dispensing arm 5.

Figure 3:
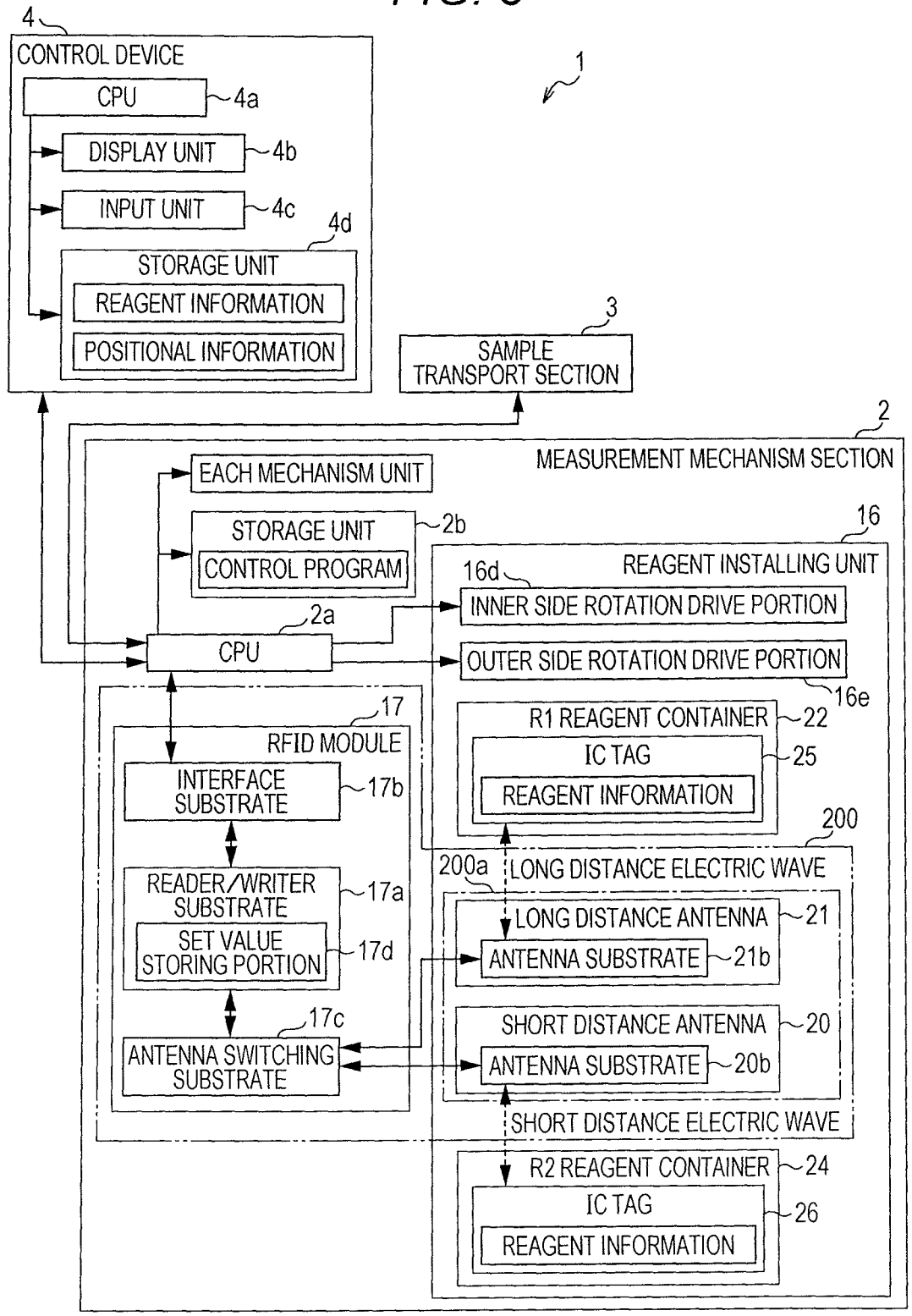
FIG. 3 is a block diagram for describing the configuration of the immune analyzer according to the first embodiment shown in FIG. 1.

As shown in FIG. 3, the control device 4 includes a CPU 4a, a display unit 4b, an input unit 4c, and a storage unit 4d. The CPU 4a causes the measurement mechanism section 2 (hereinafter described as CPU 2a) to perform the measurement based on measurement conditions and the like input by the user using the input unit 4c, and analyzing the measurement result obtained by the measurement mechanism section 2 and displaying the analysis result on the display unit 4b. The storage unit 4d includes a hard disc, and individually stores the reagent information and the positional information of each of an R1 reagent container 22, an R3 reagent container 23, and an R2 reagent container 24, to be described later. The storage unit 4d will be described in detail later.

As shown in FIG. 2, the measurement mechanism section 2 is configured by the sample dispensing arm 5, an R1 reagent dispensing arm 6, an R2 reagent dispensing arm 7, an R3 reagent dispensing arm 8, a reaction unit 9, a cuvette supplying unit 10, a primary BF separator 11, a secondary BF separator 12, a pipette tip supplying unit 13, a detector 14, an R4/R5 reagent supply unit 15, a reagent installing unit 16, and an RFID (Radio Frequency Identification) module 17.

As shown in FIG. 3, each mechanism unit (various dispensing arms, reaction unit 9, etc.) in the measurement mechanism section 2 is controlled by the CPU 2a arranged in the measurement mechanism section 2. The sample transport section 3 is also configured to be controlled by the CPU 2a. Furthermore, the measurement mechanism section 2 includes a storage unit 2b, which stores control programs causing the CPU 2a to execute the operation control of each mechanism unit of the measurement mechanism section 2.

As shown in FIG. 2, the cuvette supplying unit 10 is configured to be able to accommodate a plurality of cuvettes (not shown), and sequentially supplies the cuvettes one at a time to a sample discharging position by the sample dispensing arm 5.

The R1 reagent dispensing arm 6 aspirates the R1 reagent installed at the reagent installing unit 16, and dispenses (discharges) the aspirated R1 reagent to the cuvette mounted at the sample discharging position. The R1 reagent dispensing arm 6 also transfers the cuvette mounted at the sample discharging position to the reaction unit 9 by a catcher (not shown).

The pipette tip supplying unit 13 transports the plurality of inserted pipette tips (not shown) one at a time to the tip attaching position by the sample dispensing arm 5. The pipette tip is then attached to the distal end of the pipette of the sample dispensing arm 5 at the tip attaching position.

After the pipette tip is attached at the tip attaching position, the sample dispensing arm 5 is configured to aspirate the sample in the test tube transported to the sample aspirating position by the sample transport section 3, and dispense (discharge) the sample to the cuvette at the sample discharging position dispensed with the R1 reagent by the R1 reagent dispensing arm 6.

The R2 reagent dispensing arm 7 aspirates the R2 reagent installed in the reagent installing unit 16. The R2 reagent dispensing arm 7 is configured to dispense (discharge) the aspirated R2 reagent to the cuvette accommodating the R1 reagent and the sample.

The reaction unit 9 is formed to a substantially circular ring shape so as to surround the periphery of the reagent installing unit 16 having a substantially circular shape in plan view. The reaction unit 9 is configured to rotate in a clockwise direction, and moves the cuvette held at a cuvette holding portion 9a to each processing position where various processes (dispensing of reagent, etc.) are carried out.

The primary BF separator 11 is configured to separate (B/F separation) the non-reactive R1 reagent (unnecessary component) and the magnetic particles from the specimen in the cuvette after the cuvette accommodating the sample, the R1 reagent, and the R2 reagent is transferred from the reaction unit 9 to the primary BF separator 11 by the catcher (not shown).

The R3 reagent dispensing arm 8 is configured to aspirate the R3 reagent installed in the reagent installing unit 16. The R3 reagent dispensing arm 8 is further configured to dispense (discharge) the aspirated R3 reagent to the cuvette when the cuvette accommodating the specimen after the B/F separation by the primary BF separator 11 is transferred from the primary BF separator 11 to the reaction unit 9.

The secondary BF separator 12 is configured to separate the non-reactive R3 reagent (unnecessary component) and the magnetic particles from the specimen in the cuvette after the cuvette that accommodates the specimen after the B/F separation by the primary BF separator 11 and the R3 reagent is transferred from the reaction unit 9 to the secondary BF separator 12 by the catcher (not shown).

The R4/R5 reagent supply unit 15 is configured to dispense the R4 reagent and the R5 reagent, in order, to the cuvette accommodating the specimen after the B/F separation by the secondary BF separator 12 with a tube (not shown).

The detector 14 is arranged to measure the amount of antigen contained in the sample by obtaining the light generated in the reaction process of the labeled antibody bound to the antigen of the sample performed with a predetermined process and the light emitting substrate with a photo multiplier tube.

As shown in FIG. 2, the reagent installing unit 16 includes a housing 16a (see FIG. 4) having a substantially cylindrical shape, a lid portion 16b arranged to cover the housing 16a from the upper side, and an open/close portion 16c arranged in the lid portion 16b to be opened and closed when the user changes the R1 reagent container 22, the R3 reagent container 23, and the R2 reagent container 24. An openable/closable window (not shown) is formed at the upper surface of the lid portion 16b corresponding to the aspirating position of the R1 reagent, the R2 reagent, and the R3 reagent. The R1 reagent, the R2 reagent, and the R3 reagent are respectively aspirated by the R1 reagent dispensing arm 6, the R2 reagent dispensing arm 7, and the R3 reagent dispensing arm 8 through the window.

Figure 4:
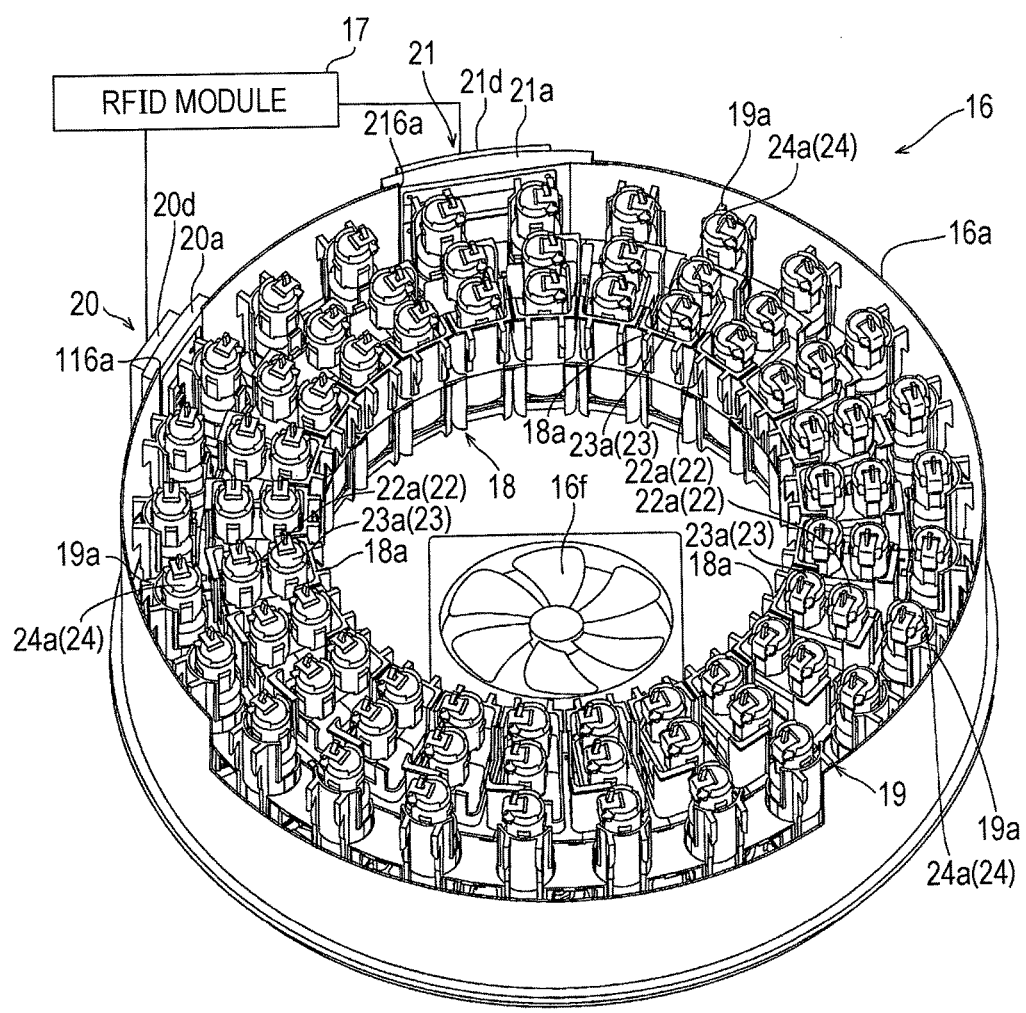
FIG. 4 is a perspective view showing the interior of a reagent installing unit of the immune analyzer according to the first embodiment shown in FIG. 1.
Figure 5:
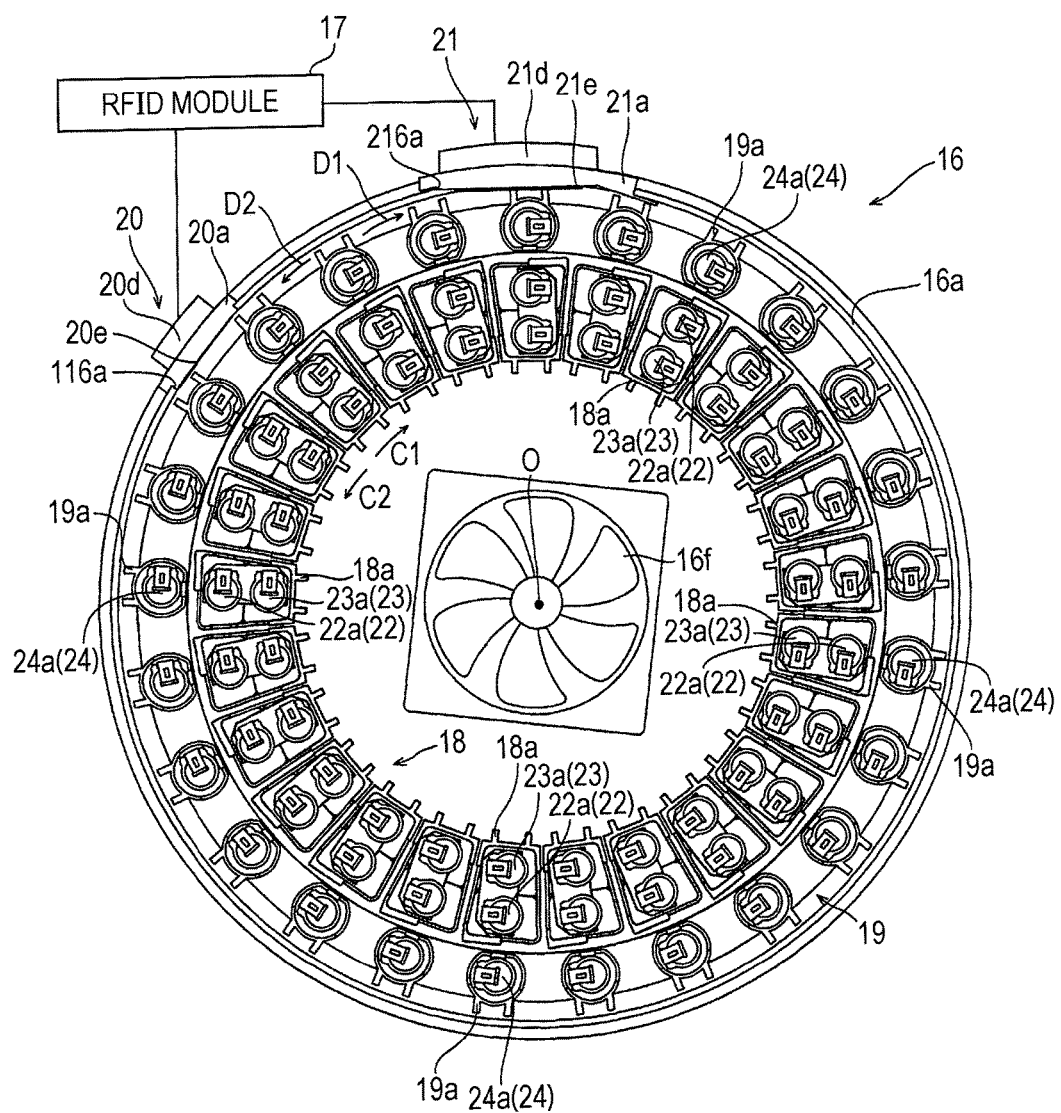
FIG. 5 is a plan view showing the interior of the reagent installing unit of the immune analyzer according to the first embodiment shown in FIG. 1.

In the first embodiment, the housing 16a of the reagent installing unit 16 includes an R1/R3 installing portion 18, an R2 installing portion 19, a short distance antenna 20, and a long distance antenna 21, as shown in FIG. 4 and FIG. 5. Specifically, as shown in FIG. 5, the R1/R3 installing portion 18 formed to a substantially circular ring shape having substantially the same center O as the center O of the housing 16a and the R2 installing portion 19 formed to a substantially circular ring shape having substantially the same center O as the center O of the housing 16a are arranged inside the housing 16a in plan view. The R1/R3 installing portion 18 is arranged on the inner peripheral side (center O side) of the R2 installing portion 19.

Figure 6:
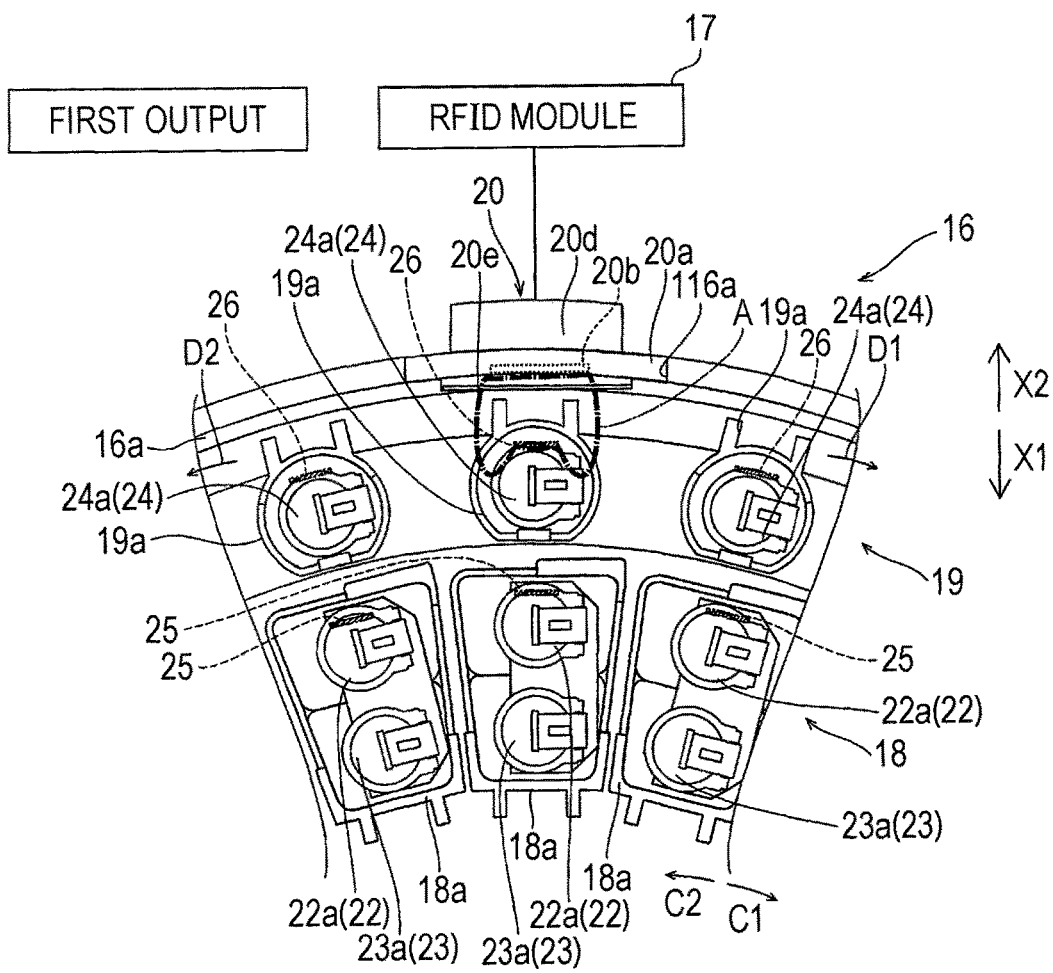
FIG. 6 is an enlarged plan view showing a state of when reading an IC tag of an R2 reagent container of the reagent installing unit according to the first embodiment shown in FIG. 1.
Figure 7:
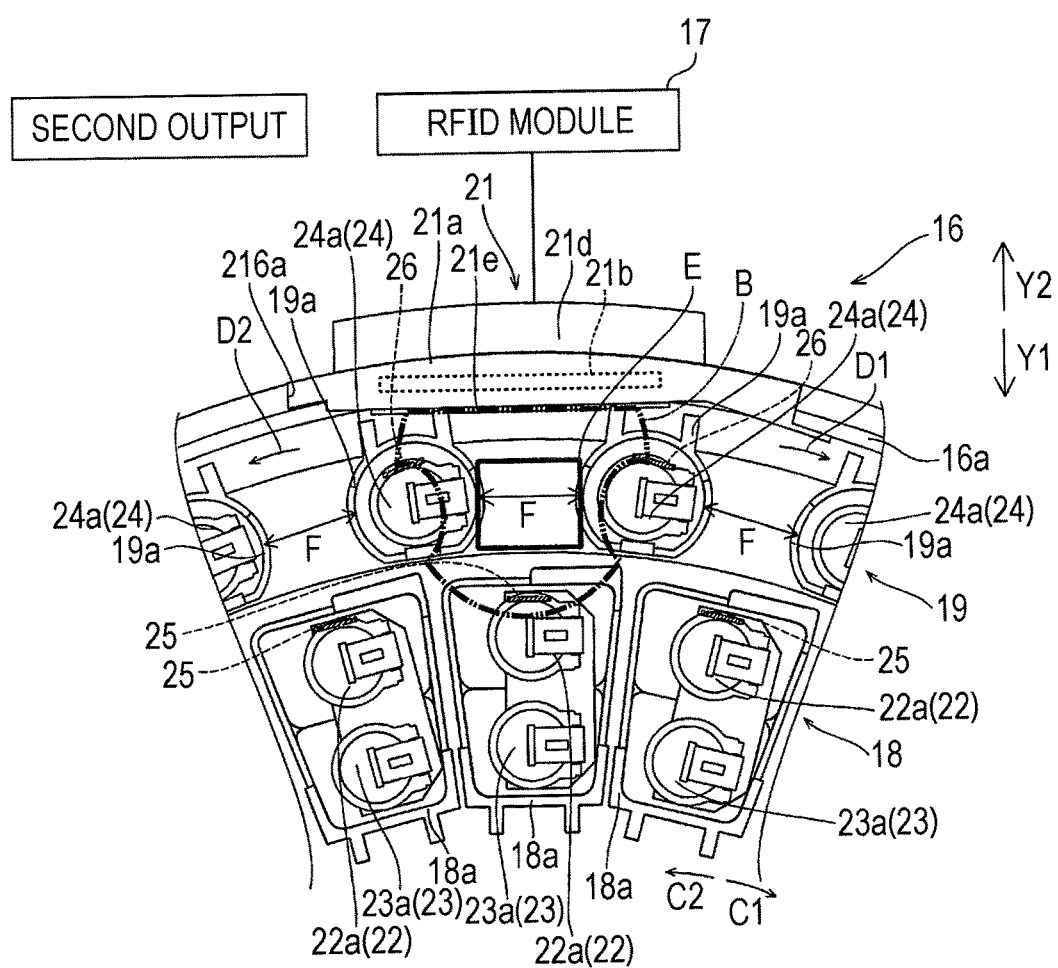
FIG. 7 is an enlarged plan view showing a state of when reading an IC tag of an R1 reagent container of the reagent installing unit according to the first embodiment shown in FIG. 1.

The short distance antenna 20 and the long distance antenna 21 are attached to the housing 16a of the reagent installing unit 16. Specifically, as shown in FIG. 5, cutouts 116a and 216a are formed at two areas with a predetermined distance (predetermined rotation angle interval) of the side walls arranged in a circular ring shape configuring the housing 16a. The cutouts 116a and 216a are formed by cutting one part of the housing 16a to the lower side from the upper end. As shown in FIG. 6, the cutout 116a of the housing 16a is fixed with a resin stopping portion 20a of the short distance antenna 20 by being stopped. As shown in FIG. 7, the cutout 216a of the housing 16a is fixed with a resin stopping portion 21a of the long distance antenna 21 by being stopped. As shown in FIG. 5, the short distance antenna 20 and the long distance antenna 21 are both arranged on the outer peripheral side of the R2 installing portion 19.

The reagent installing unit 16 includes an inner side rotation drive portion 16d (see FIG. 3) for rotating the R1/R3 installing portion 18 in the direction of the arrow C1 and in the direction of the arrow C2 with the center O as the center of rotation, and an outer side rotation drive portion 16e (see FIG. 3) for rotating the R2 installing portion 19 in the direction of the arrow D1 and in the direction of the arrow D2 with the center O as the center of rotation. The inner side rotation drive portion 16d and the outer side rotation drive portion 16e are configured such that the drive is individually controlled by the CPU 2a. A peltier element (not shown) and a fan 16f for cooling the R1 reagent, the R2 reagent, and the R3 reagent are arranged at the center O of the bottom of the housing 16a. This cooling may cause dew condensation in the reagent installing unit 16.

Figure 8:
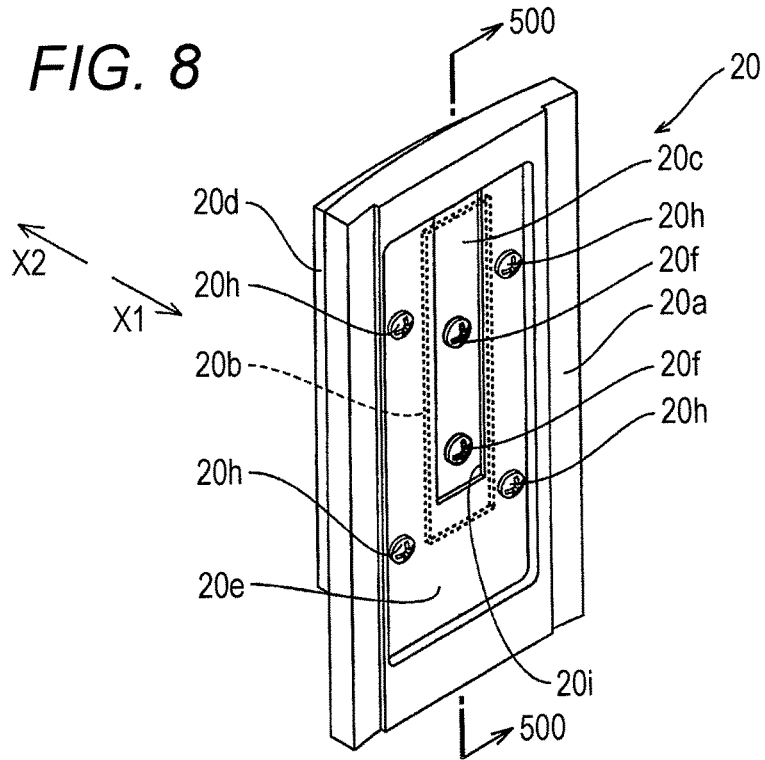
FIG. 8 is a perspective view showing a short distance antenna of the reagent installing unit according to the first embodiment shown in FIG. 1.
Figure 9:
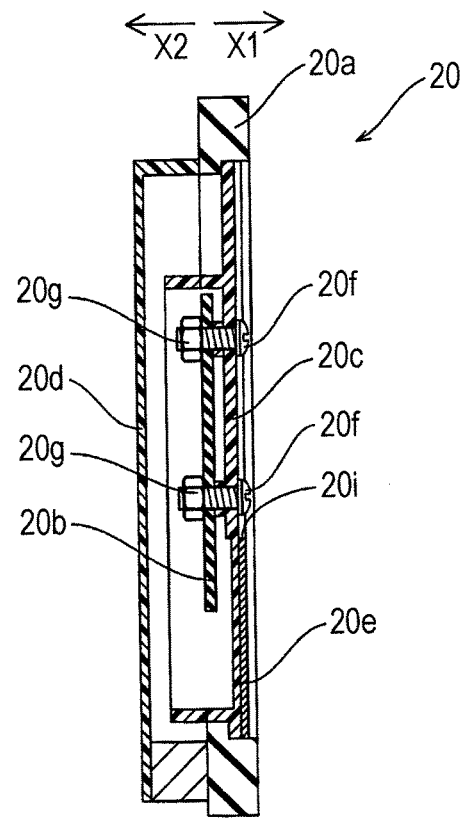
FIG. 9 is a cross-sectional view showing the short distance antenna of the reagent installing unit along a line 500-500 of FIG. 8.

As shown in FIG. 8 and FIG. 9, the short distance antenna 20 includes an antenna substrate 20b, a substrate attachment portion 20c interiorly fixed with the antenna substrate 20b, a lid member 20d for covering the antenna substrate 20b from the outer side (side in the direction of the arrow X2), and a metal plate 20e attached to the surface on the side opposite to (side in the direction of the arrow X1) the antenna substrate 20b of the substrate attachment portion 20c in addition to the stopping portion 20a.

Figure 10:
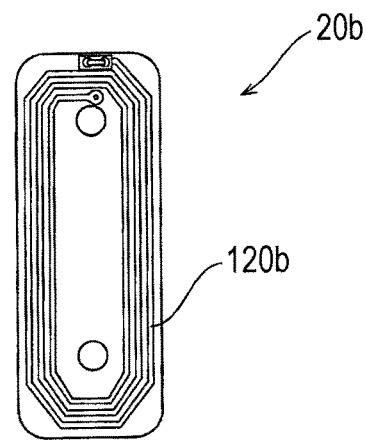
FIG. 10 is a plan view showing an antenna substrate of the short distance antenna according to the first embodiment shown in FIG. 1.

As shown in FIG. 10, the antenna substrate 20b of the short distance antenna 20 is configured by forming a coil-shaped antenna wiring 120b on the surface (see FIG. 9) on the side in the direction of the arrow X1 of the plate-shaped substrate. The electric wave can be transmitted and received through the coil-shaped antenna wiring 120b.

Figure 11:
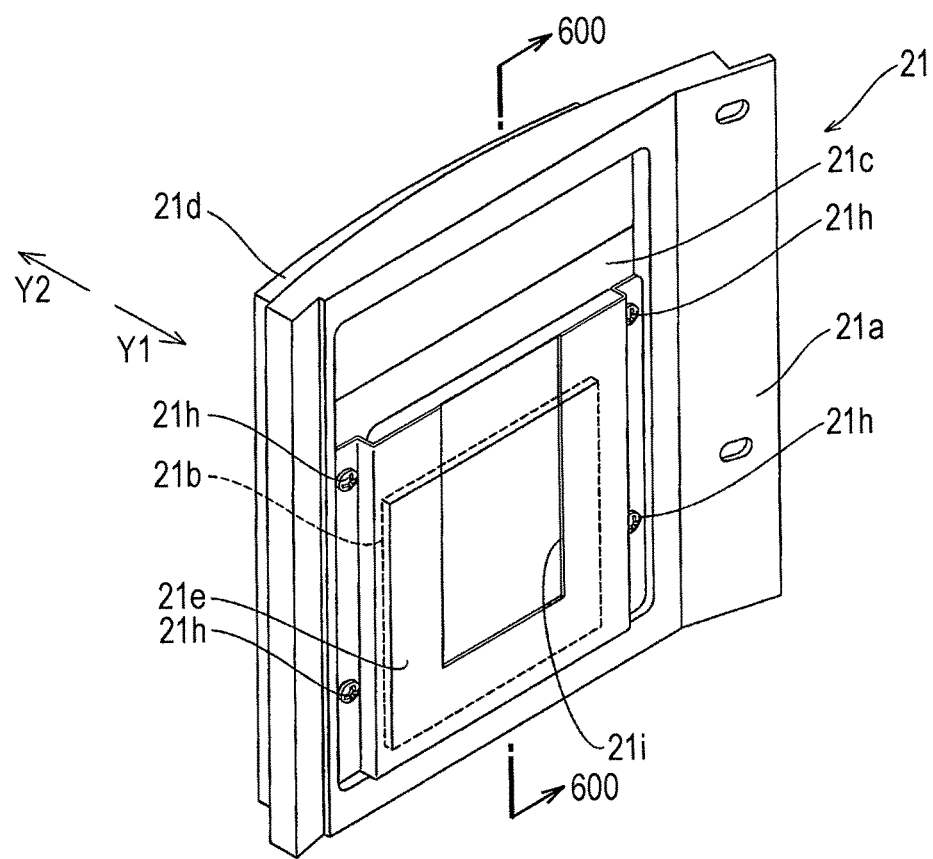
FIG. 11 is a perspective view showing a long distance antenna of the reagent installing unit according to the first embodiment shown in FIG. 1.
Figure 12:
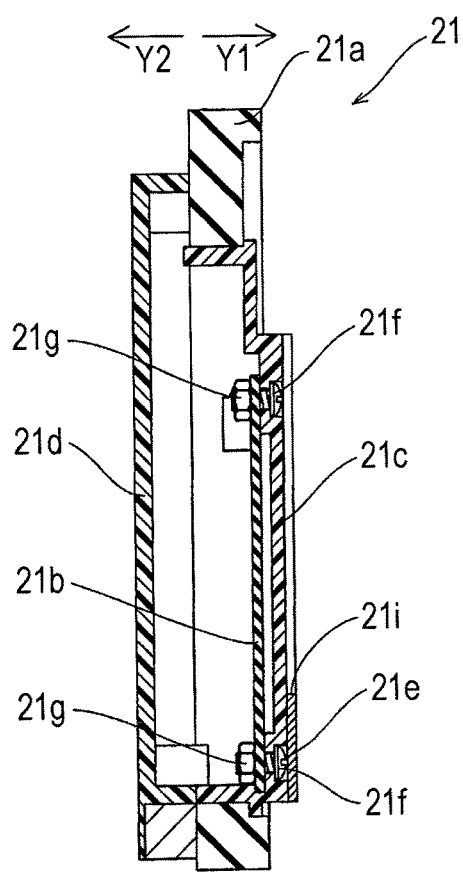
FIG. 12 is a cross-sectional view showing the long distance antenna of the reagent installing unit along a line 600-600 of FIG. 11.

As shown in FIG. 11 and FIG. 12, the long distance antenna 21 includes an antenna substrate 21b, a substrate attachment portion 21c interiorly fixed with the antenna substrate 21b, a lid member 21d for covering the antenna substrate 21b from the outer side (side in the direction of the arrow Y2), and a metal plate 21e attached to the surface on the side opposite to (side in the direction of the arrow Y1) the antenna substrate 21b of the substrate attachment portion 21c in addition to the stopping portion 21a.

Figure 13:
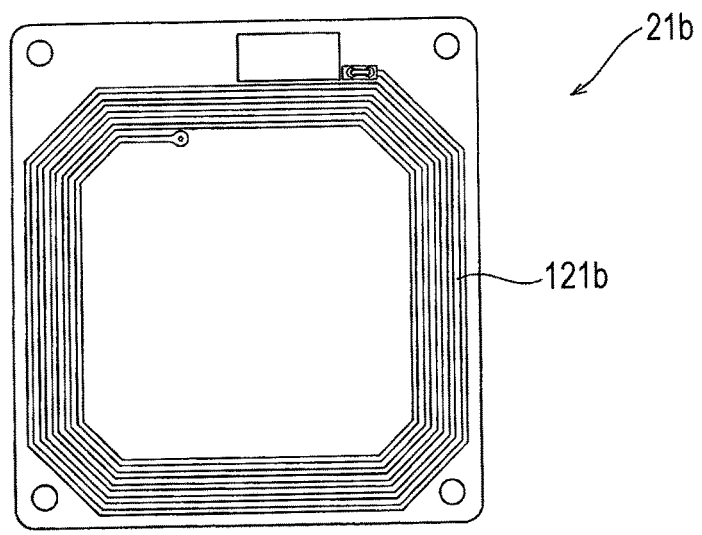
FIG. 13 is a plan view showing an antenna substrate of the long distance antenna according to the first embodiment shown in FIG. 1.

As shown in FIG. 13, the antenna substrate 21b of the long distance antenna 21 is configured by forming a coil-shaped antenna wiring 121b on the surface (see FIG. 12) on the side in the direction of the arrow Y1 of the plate-shaped substrate. The electric wave can be transmitted and received through the coil-shaped antenna wiring 121b.

As shown in FIG. 6, the antenna substrate 20b is arranged inside the substrate attachment portion 20c such that the surface on the side in the direction of the arrow X1 of the antenna substrate 20b faces the center O (see FIG. 5) of the housing 16a, and as shown in FIG. 7, the antenna substrate 21b is arranged inside the substrate attachment portion 21c such that the surface on the side in the direction of the arrow Y1 of the antenna substrate 21b faces the center O (see FIG. 5) of the housing 16a. Therefore, as shown in FIG. 6 and FIG. 7, the antenna substrates 20b and 21b are configured so as to be able to emit the read electric wave and the write electric wave towards the inner side (towards center O of FIG. 5) of the reagent installing unit 16, and so as to be able to receive response electric waves emitted from the IC tags 25 and 26, to be described later, in response to the read electric wave. The antenna substrates 20b and 21b are connected to an antenna switching substrate 17c, to be described later, of the RFID module 17.

In the first embodiment, the number of windings of the coil in the antenna wiring 121b (see FIG. 13) of the antenna substrate 21b of the long distance antenna 21 is configured to become greater than the number of windings of the coil in the antenna wiring 120b (see FIG. 10) of the antenna substrate 20b of the short distance antenna 20. Furthermore, the power (first output) output from the reader/writer substrate 17a to the antenna substrate 20b of the short distance antenna 20 through the antenna switching substrate 17c, to be described later, is configured to become smaller than the power (second output) output from the reader/writer substrate 17a to the antenna substrate 21b of the long distance antenna 21 through the antenna switching substrate 17c. Therefore, the short distance antenna 20 is configured to emit a short distance read electric wave and a short distance write electric wave in the range of A, as shown in FIG. 6. Furthermore, as shown in FIG. 7, the long distance antenna 21 is configured to emit a long distance read electric wave and a long distance write electric wave in the range of B, which is greater than the range A. As a result, the read range and the write range of the short distance antenna 20 is configured to be smaller than the read range and the write range of the long distance antenna 21.

The substrate attachment portion 20c and the lid member 20d of the short distance antenna 20 are both made of resin capable of transmitting the electric wave. As shown in FIG. 9, the substrate attachment portion 20c and the lid member 20d are arranged to protect the antenna substrate 20b from dew condensation and the like, and hence the antenna substrate 20b is isolated from the outside by the substrate attachment portion 20c and the lid member 20d. Similarly, the substrate attachment portion 21c and the lid member 21d of the long distance antenna 21 are both made of resin capable of transmitting the electric wave. As shown in FIG. 12, the substrate attachment portion 21c and the lid member 21d are arranged to protect the antenna substrate 21b from dew condensation and the like, and hence the antenna substrate 21b is isolated from the outside by the substrate attachment portion 21c and the lid member 21d.

As shown in FIG. 9, the antenna substrate 20b is fixed to the substrate attachment portion 20c with a screw 20f and a nut 20g, and as shown in FIG. 12, the antenna substrate 21b is fixed to the substrate attachment portion 21c with a screw 21f and a nut 21g.

The metal plates 20e and 21e are both made of aluminum plate materials capable of absorbing electric waves (read electric wave, write electric wave, and response electric wave). As shown in FIG. 8, the metal plate 20e is fixed to the substrate attachment portion 20c with a screw 20h and a nut (not shown) so as to be arranged on the surface on the side of the direction indicated with the arrow X1 of the substrate attachment portion 20c. Similarly, as shown in FIG. 11, the metal plate 21e is fixed to the substrate attachment portion 21c with a screw 21h and a nut (not shown) so as to be arranged on the surface on the side of the direction indicated with the arrow Y1 of the substrate attachment portion 21c.

As shown in FIG. 8 and FIG. 11, the metal plates 20e and 21e are respectively formed with substantially U-shaped cutouts 20i and 21i. The antenna substrates 20b and 21b are configured to emit the electric wave towards the inner side of the reagent installing unit 16 (direction of the arrow X1 and the direction of the arrow Y1) through the cutouts 20i and 21i, and to absorb the electric wave of the antenna substrates 20b and 21b that does not pass through the cutouts 20i and 21i with the metal plates 20e and 21e. In other words, the metal plate 20e limits the read range and the write range of the short distance antenna 20 (antenna substrate 20b) by limiting the range of the electric wave emitted from the antenna substrate 20b and the range of the electric wave received by the antenna substrate 20b. Similarly, the metal plate 21e limits the read range and the write range of the long distance antenna 21 (antenna substrate 21b) by limiting the range of the electric wave emitted from the antenna substrate 21b and the range of the electric wave received by the antenna substrate 21b.

As shown in FIG. 5, the R1/R3 installing portion 18 includes twenty-five R1/R3 holding members 18a, which are made of resin capable of transmitting the electric wave, arranged at an equal angle (about 14.4 degrees). Each R1/R3 holding member 18a holds the R1 reagent container 22 for accommodating the R1 reagent (first reagent) containing the capture antibody, and the R3 reagent container 23 for accommodating the R3 reagent containing the labeled body. In other words, twenty-five R1 reagent containers 22 are arranged at equal angle (about 14.4 degrees) in the R1/R3 installing portion 18. The R1/R3 holding member 18a is configured such that the R1 reagent container 22 is held on the outer side (R2 installing portion 19 side) and the R3 reagent container 23 is held on the inner side (center O side).

The R2 installing portion 19 includes twenty-five R2 holding members 19a, which are made of resin capable of transmitting the electric wave, arranged at an equal angle (about 14.4 degrees). Each R2 holding member 19a holds the R2 reagent container 24 for accommodating the R2 reagent (second reagent) containing the magnetic particles. In other words, twenty-five R2 reagent containers 24 are arranged at equal angle (about 14.4 degrees) in the R2 installing portion 19. The R1 reagent container 22, the R3 reagent container 23, and the R2 reagent container 24 are configured so as to be installable and replaceable by the user.

Figure 14:
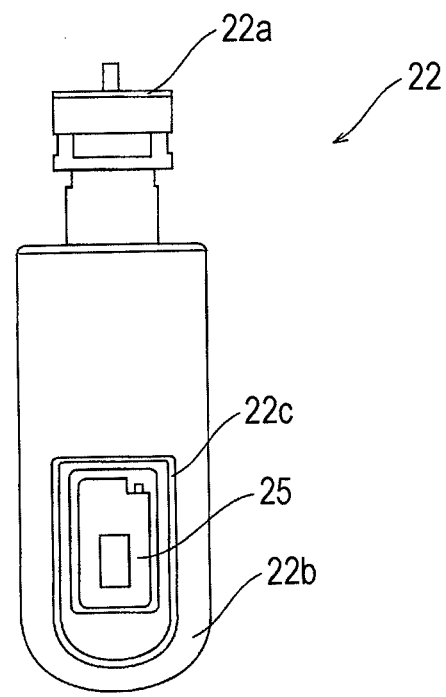
FIG. 14 is a side view showing the side on the direction of the arrow X2 of the R1 reagent container of the reagent installing unit according to the first embodiment shown in FIG. 1.
Figure 15:
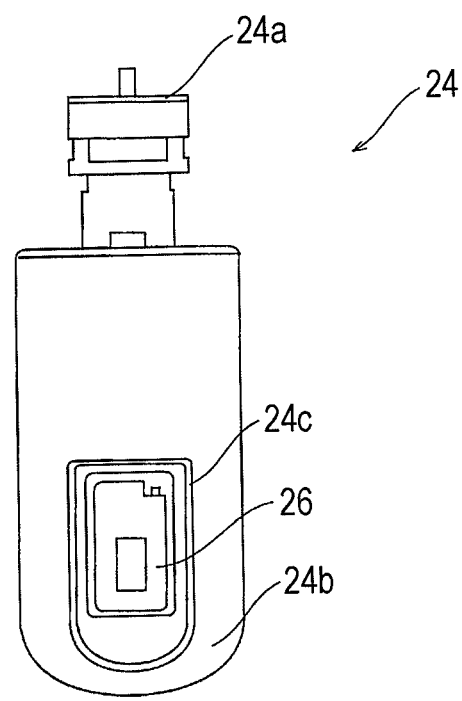
FIG. 15 is a side view showing the side on the direction of the arrow Y2 of the R2 reagent container of the reagent installing unit according to the first embodiment shown in FIG. 1.

As shown in FIG. 14, the R1 reagent container 22 is formed with a lid 22a that opens and closes when aspirating the R1 reagent, and a reagent accommodating portion 22b for accommodating the R1 reagent. As shown in FIG. 15, the R2 reagent container 24 is formed with a lid 24a that opens and closes when aspirating the R2 reagent, and a reagent accommodating portion 24b for accommodating the R2 reagent. As shown in FIG. 6 and FIG. 7, the R3 reagent container 23 and the R1 reagent container 22 have substantially a similar shape, and the R3 reagent container 23 is formed with a lid 23a that opens and closes when aspirating the R3 reagent, and a reagent accommodating portion (not shown) for accommodating the R3 reagent. The lids 22a and 23a are configured to open and close with the rotation of the R1/R3 installing portion 18, and the lid 24a is configured to open and close with the rotation of the R2 installing portion 19.

As shown in FIG. 14, an IC tag attachment portion 22c, where the IC tag 25 is to be attached, is formed on the side surface arranged on the outer side (direction of arrow X2 in FIG. 6) of the reagent accommodating portion 22b of the R1 reagent container 22. As shown in FIG. 15, an IC tag attachment portion 24c, where the IC tag 26 is to be attached, is formed on the side surface arranged on the outer side (direction of arrow Y2 in FIG. 7) of the reagent accommodating portion 24b of the R2 reagent container 24. In other words, the IC tag 26 of the R2 reagent container 24 is attached to face the outer side (direction of the arrow X2) of the reagent installing unit 16 when the R2 reagent container 24 is arranged in the R2 installing portion 19, as shown in FIG. 6, and the IC tag 25 of the R1 reagent container 22 is attached to face the outer side (direction of the arrow Y2) of the reagent installing unit 16 when the R1 reagent container 22 is arranged in the R1/R3 installing portion 18, as shown in FIG. 7. An IC tag is not attached to the side surface of the R3 reagent container 23, as opposed to the R1 reagent container 22.

The IC tag 25 records the reagent information of the R1 reagent of the R1 reagent container 22, and the reagent information of the R3 reagent of the R3 reagent container 23 held in the R1/R3 holding member 18a common with the R1 reagent container 22. The IC tag 26 records the reagent information of the R2 reagent of the R2 reagent container 24.

Figure 16:
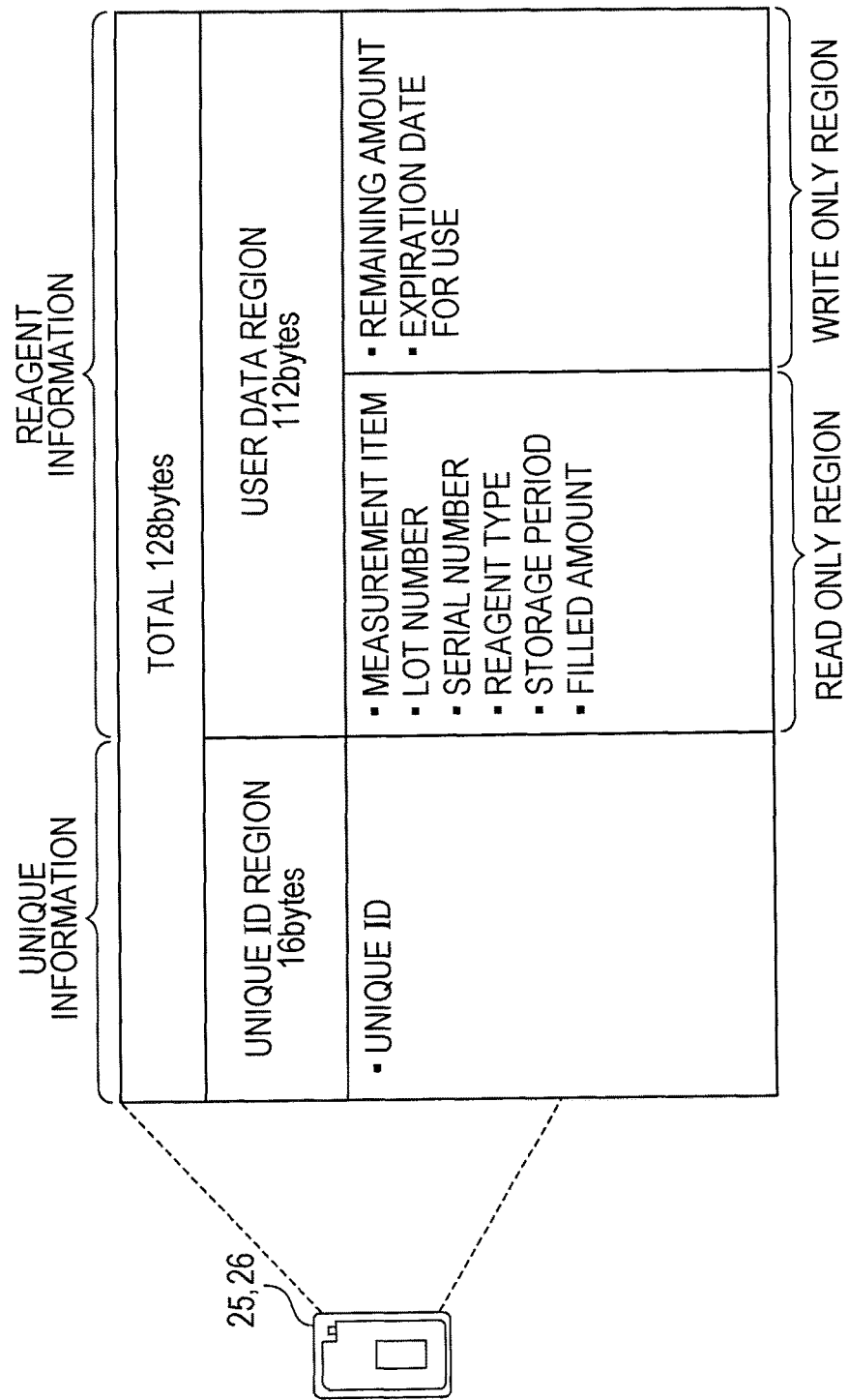
FIG. 16 is a conceptual view showing the unique information and the reagent information stored in the IC tag according to the first embodiment shown in FIG. 1.

As shown in FIG. 16, the IC tags 25 and 26 are configured to be able to store 128 bytes of information. Among the storage capacity of 128 bytes, 16 bytes are assigned for the unique ID region indicating the unique information, and 112 bytes are assigned for the user data region indicating the reagent information. The unique ID region is the region where the unique ID for individually identifying the IC tags 25 and 26 is recorded, and only read can be carried out. The user data region is the region where the user can freely write information. The user data region is set with a region (read only region) where only read is carried out and write is not carried out, and a region (writeable region) where both read and write are carried out.

The unique ID is used when the CPU 2a encrypts the reagent information. Thus, the reagent information cannot be decrypted if the unique ID is different even if the reagent information is duplicated to a different IC tag, and hence the reagent information and the reagent of the reagent container can be suppressed from being wrongly communicated.

The measurement item, the lot number, the serial number, the reagent type (type specifying information), the storage period, and the filled amount regarding the reagent container (R1 reagent container 22 or R2 reagent container 24) given the IC tag (IC tag 25 or 26) are recorded in the read only region, and the remaining amount and the expiration date for use are written in the writable region. The IC tag 25 also records the information regarding the R3 reagent container 23. The information is not written to the writable region of the IC tag 25 attached to the R1 reagent container 22 installed in the R1/R3 installing portion 18 for the first time, and the IC tag 26 attached to the R2 reagent container 24 installed in the R2 installing portion 19 for the first time.

The measurement item shows the measurement item performed with the reagent accommodated in the reagent container attached with the IC tag. The reagent type shows whether the reagent container attached with the IC tag is the R1 reagent container 22 or the R2 reagent container 24. The storage period shows the period the reagent can be stored. The filled amount shows the number of measurements that can be carried out with the reagent. The remaining amount shows the number of measurements that can be carried out with the reagent. The expiration date for use shows the date until the reagent can be used. The expiration date for use is set when the relevant reagent starts to be used.

In the first embodiment, the IC tag 26 of the R2 reagent container 24 is configured so that read and write are carried out at the front surface position (facing position) of the short distance antenna 20, as shown in FIG. 6. In this case, the IC tag 26 is configured to emit the response electric wave including the reagent information recorded on the IC tag 26 based on the short distance read electric wave in the range A (thick chain dashed line) emitted from the short distance antenna 20. The IC tag 26 is also configured to rewrite the recorded reagent information to the new reagent information contained in the short distance write electric wave based on the short distance write electric wave in the range A emitted from the short distance antenna 20.

Figure 17:
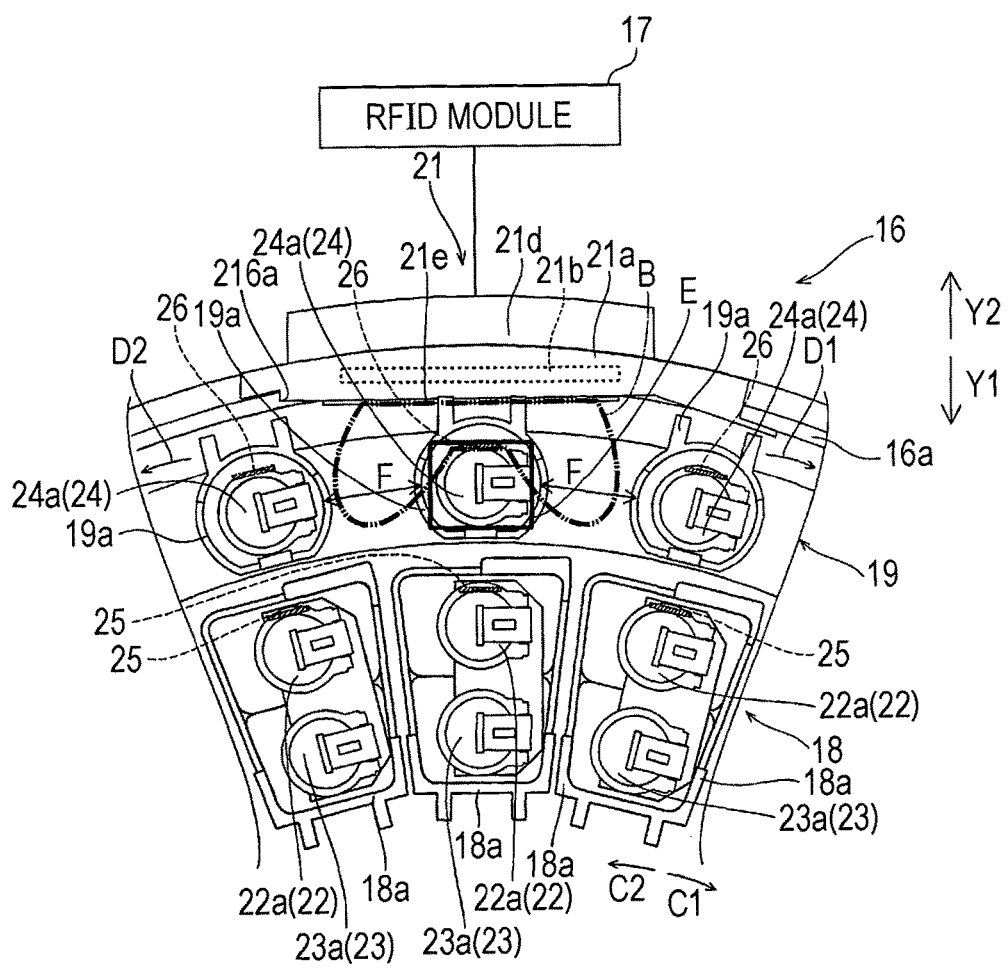
FIG. 17 is an enlarged plan view showing a state in which the R2 reagent container of the reagent installing unit is positioned in region E according to the first embodiment shown in FIG. 1.

As shown in FIG. 7 and FIG. 17, the IC tag 25 of the R1 reagent container 22 is configured so that read and write are carried out at the front surface position of the long distance antenna 21. In this case, the IC tag 25 is configured to emit the response electric wave containing the reagent information recorded on the IC tag 25 based on the long distance read electric wave in the range B (thick chain double dashed line) emitted from the long distance antenna 21. The IC tag 25 is also configured to rewrite the recorded reagent information to new reagent information contained in the long distance write electric wave based on the long distance write electric wave in the range B emitted from the long distance antenna 21.

The interval between the adjacent R1/R3 holding members 18a and the interval between the adjacent R2 holding members 19a, the range A and the range B are set so that read and write are carried out on specific IC tags 25 and 26, and read and write are not carried out on the other IC tags 25 and 26. The reagent information is recorded in the IC tags 25 and 26 in an encrypted state.

As shown in FIG. 3, respective reagent information of the twenty-five R1 reagent containers 22, the twenty-five R2 reagent containers 24, and the twenty-five R3 reagent containers 23 are individually stored in the storage unit 4d of the control device 4 apart from the IC tags 25 and 26. The storage unit 4d stores the respective initial position of the twenty-five R1 reagent containers 22, the twenty-five R3 reagent containers 23, and the twenty-five R2 reagent containers 24, and the rotation angle from the respective initial position of the R1/R3 installing portion 18 and the R2 installing portion 19 as positional information. The storage unit 4d thus stores the positional information and the reagent information of twenty-five R1 reagent containers 22, the twenty-five R3 reagent containers 23, and the twenty-five R2 reagent containers 24 in a corresponded state. The reagent information is stored in the storage unit 4d of the control device 4 in the decrypted state.

When the power supply (not shown) of the immune analyzer 1 is turned ON, the IC tags (IC tags 25 and 26) of all the reagent containers installed in the reagent installing unit 16 are read, and the positional information and the reagent information of each reagent container are acquired. If the reagent infoimation is stored in the storage unit 4d, the CPU 4a of the control device 4 updates the reagent information stored in the storage unit 4d to the reagent infoimation acquired from the IC tag when the power supply is turned ON. Thus, even if the R1 reagent container 22, the R3 reagent container 23, and the R2 reagent container 24 are respectively changed to a new R1 reagent container 22, R3 reagent container 23, and R2 reagent container 24 while the power supply of the immune analyzer 1 is turned OFF, the reagent information stored in the storage unit 4d of the control device 4 can be updated to the information of the reagent currently installed at the reagent installing unit 16.

As shown in FIG. 2, the RFID module 17 is arranged exterior to the reagent installing unit 16, and includes a reader/writer substrate 17a, an interface substrate 17b for intermediating the reader/writer substrate 17a and the CPU 2a, and an antenna switching substrate 17c, as shown in FIG. 3.

The reader/writer substrate 17a is configured to emit the long distance read electric wave (short distance read electric wave) and the long distance write electric wave (short distance write electric wave) having a frequency band of about 13.56 MHz from the long distance antenna 21 (short distance antenna 20) based on an instruction from the CPU 2a. Furthermore, the reader/writer substrate 17a is configured to acquire the reagent information from the response electric wave emitted from the IC tags 25 and 26 in response to the long distance read electric wave (short distance read electric wave) and received by the short distance antenna 20 and the long distance antenna 21, and to output the reagent information to the CPU 2a.

The reader/writer substrate 17a includes a set value storing portion 17d for storing a set value corresponding to the antenna substrate 20b, a set value corresponding to the antenna substrate 21b, and a set value of transmission output to the antenna substrate, where such set values are set by the CPU 2a. The antenna switching substrate 17c receives the signal corresponding to the set value stored in the set value storing portion 17d from the reader/writer substrate 17a, and switching to transmit and receive the read electric wave and the write electric wave using either the short distance antenna 20 or the long distance antenna 21 based on the received signal.

As shown in FIG. 3, in the first embodiment, the RFID module 17, the short distance antenna 20 and the long distance antenna 21 configure a reagent information reading unit 200 for reading the reagent information recorded on the IC tags 25 and 26. The short distance antenna 20 and the long distance antenna 21 respectively functions as an electric wave emitting portion 200a for emitting electric wave to the IC tags 26 and 25.

Figure 18:
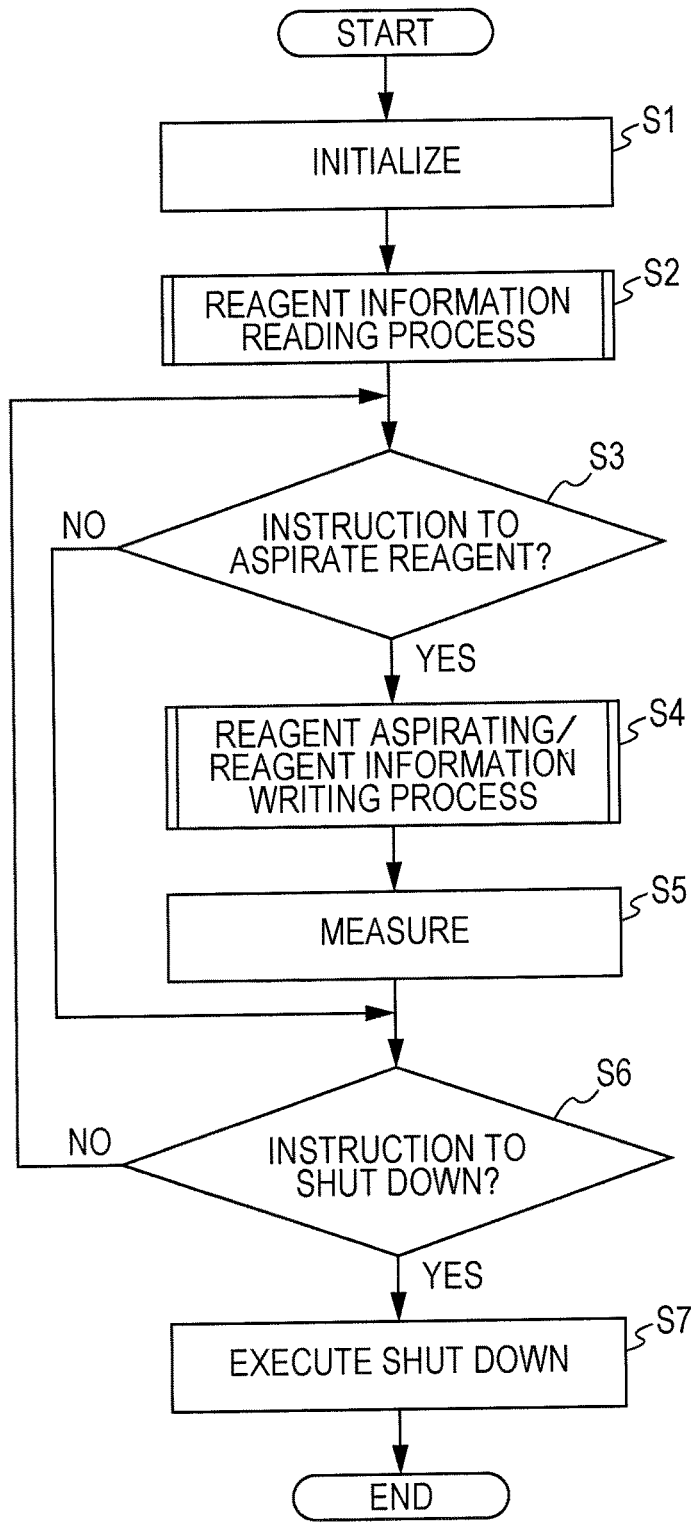
FIG. 18 is a flowchart showing the measurement operation of the immune analyzer according to the first embodiment shown in FIG. 1.

The measurement operation of the immune analyzer 1 (measurement mechanism section 2) according to the first embodiment of the present invention will now be described with reference to FIG. 3 and FIG. 18.

First, when the power supply of the measurement mechanism section 2 is turned ON, the CPU 2a of the measurement mechanism section 2 initializes the program in step S1 and executes an initialization process such as operation check of each unit of the measurement mechanism section 2.

Thereafter, the reagent information reading process is performed in step S2. The reagent information reading process will be described in detail later.

In step S3, whether or not a measurement instruction by the user is made is determined by the CPU 2a. The measurement instruction by the user is transmitted to the CPU 2a through the control device 4 (see FIG. 3). If determined that the measurement instruction by the user is not made, the process proceeds to step S6.

If determined that the measurement instruction by the user is made in step S3, the reagent aspirating/reagent information writing process is carried out by the CPU 2a in step S4. The reagent aspirating/reagent information writing process will be described in detail later.

Subsequently, the sample is measured in the measurement mechanism section 2 in step S5. In step S6, whether or not the instruction to shut down by the user is made is determined by the CPU 2a. The process returns to step S3 if determined that the instruction of shutdown is not made. If determined that the instruction of shutdown is made, the shutdown of the measurement mechanism section 2 is carried out by the CPU 2a in step S7. The measurement operation of the CPU 2a of the measurement mechanism section 2 is terminated in such manner.

With reference to FIG. 6, FIG. 7, FIG. 17, and FIG. 19, the reagent information reading process of the immune analyzer 1 according to the first embodiment of the present invention shown in step S2 of FIG. 18 will be described in detail.

First, in step S201, whether or not the IC tag of the read target is the IC tag 25 of the R1 reagent container 22 is determined by the CPU 2a. If the IC tag of the read target is the IC tag 25 of the R1 reagent container 22, the process proceeds to step S202. If determined that the IC tag of the read target is the IC tag 26 of the R2 reagent container 24, the process proceeds to step S206.

In step S202, the antenna that emits the read electric wave is set to the long distance antenna 21 by the CPU 2a. In other words, the set value corresponding to the antenna substrate 21b of the long distance antenna 21 and the set value of the transmission output corresponding to the antenna substrate 21b are set in the set value storing portion 17d of the reader/writer substrate 17a by the CPU 2a.

Thereafter, in step S203, the R1/R3 installing portion 18 is rotated in the direction of the arrow C1 or the direction of the arrow C2 (see FIG. 17) so that the IC tag 25 of the read target is positioned at the position opposing the long distance antenna 21 by the CPU 2a.

In step S204, whether or not the R2 reagent container 24 is positioned in the region E (see FIG. 17) in the vicinity of the position opposing the long distance antenna 21 is determined by the CPU 2a. In this case, whether or not the R2 reagent container 24 is positioned in the region E is determined based on the positional information of the R2 reagent container 24. If the R2 reagent container 24 is positioned in the region E, the read and write of the IC tag 25 may not be carried out even if the long distance antenna 21 emits the long distance read electric wave and the long distance write electric wave in the range B (see FIG. 17) as the electric wave is absorbed by the R2 reagent accommodated in the R2 reagent container 24. Thus, if determined that the R2 reagent container 24 is positioned in the region E, in step S205, the R2 installing portion 19 is rotated in the direction of the arrow D1 or the direction of the arrow D2 (see FIG. 17) so that the R2 reagent container 24 positioned in the region E is evacuated from the region E by the CPU 2a. Thus, as shown in FIG. 7, the gap F between the adjacent R2 reagent containers 24 and the IC tag 25 of the read target are arranged at the position opposing the long distance antenna 21, and the IC tag 26 of the R2 reagent container 24 is arranged at the position not opposing the long distance antenna 21. The process then proceeds to step S208. If determined that none of the R2 reagent containers 24 is positioned in the region E in step S204, the process proceeds to step S208.

If determined that the IC tag of the read target is the IC tag 26 of the R2 reagent container 24 in step S201, the antenna that emits the read electric wave is set to the short distance antenna 20 by the CPU 2a in step S206. In other words, the set value corresponding to the antenna substrate 20b of the short distance antenna 20 and the set value of the transmission output corresponding to the antenna substrate 20b are set in the set value storing portion 17d of the reader/writer substrate 17a by the CPU 2a.

Thereafter, in step S207, the R2 installing portion 19 is rotated in the direction of the arrow D1 or the direction of the arrow D2 (see FIG. 6) so that the IC tag 26 of the read target is positioned at the position opposing the short distance antenna 20 by the CPU 2a. The process then proceeds to step S208.

In step S208, the long distance read electric wave in the range B (short distance read electric wave in the range A) is emitted from the long distance antenna 21 (short distance antenna 20) to the IC tag 25 of the R1 reagent container 22 (IC tag 26 of the R2 reagent container 24) of the read target by the control of the CPU 2a, the reader/writer substrate 17a, and the antenna switching substrate 17c.

Thereafter, in step S209, whether or not the response electric wave emitted from the IC tag 25 or 26 in correspondence to the long distance read electric wave or the short distance read electric wave is received within a predetermined time by the long distance antenna 21 (short distance antenna 20) is determined by the CPU 2a. In other words, whether or not the reagent information acquired by the reader/writer substrate 17a of the RFID module 17 based on the response electric wave received from the long distance antenna 21 (short distance antenna 20) is output to the CPU 2a within a predetermined time is determined by the CPU 2a. If determined that the long distance antenna 21 (short distance antenna 20) did not receive the response electric wave within a predetermined time, the read error information is transmitted to the control device 4 by the CPU 2a in step S210. A notification that reading of the reagent information of the reagent container positioned at a predetermined position (reagent information of the reagent container of the read target) failed is displayed on the display unit 4b of the control device 4. The process then proceeds to step S213.

If determined that the long distance antenna 21 (short distance antenna 20) received the response electric wave within a predetermined time in step S209, whether or not the reagent information contained in the response electric wave received by the long distance antenna 21 (short distance antenna 20) is the reagent information of the read target is determined by the CPU 2a in step S211. In this case, the CPU 2a determines whether or not the reagent information of the read target based on the reagent type (type specifying information) obtained from the response electric wave. If determined that the reagent information contained in the response electric wave is not the reagent information of the read target, the process proceeds to step S210.

If determined that the reagent information contained in the response electric wave is the reagent information of the read target, the reagent information of the read target contained in the response electric wave is transmitted from the CPU 2a to the control device 4 in step S212. When the long distance antenna 21 (short distance antenna 20) receives a plurality of response electric waves, and the reagent information of the read target exists in the plurality of response electric waves, only the reagent information of the read target is transmitted to the control device 4. In the control device 4, the reagent information of the storage unit 4d is updated based on the reagent information received from the CPU 2a. The process then proceeds to step S213.

Finally, in step S213, whether or not the reading of all twenty-five IC tags 25 and twenty-five IC tags 26 is completed is determined by the CPU 2a. If determined that the reading is not completed, the process returns to step S201 and the reading of a new IC tag is carried out. If determined that all the reading is completed, the reagent information reading process is terminated, and the process proceeds to step S3 shown in FIG. 18.

Figure 20:
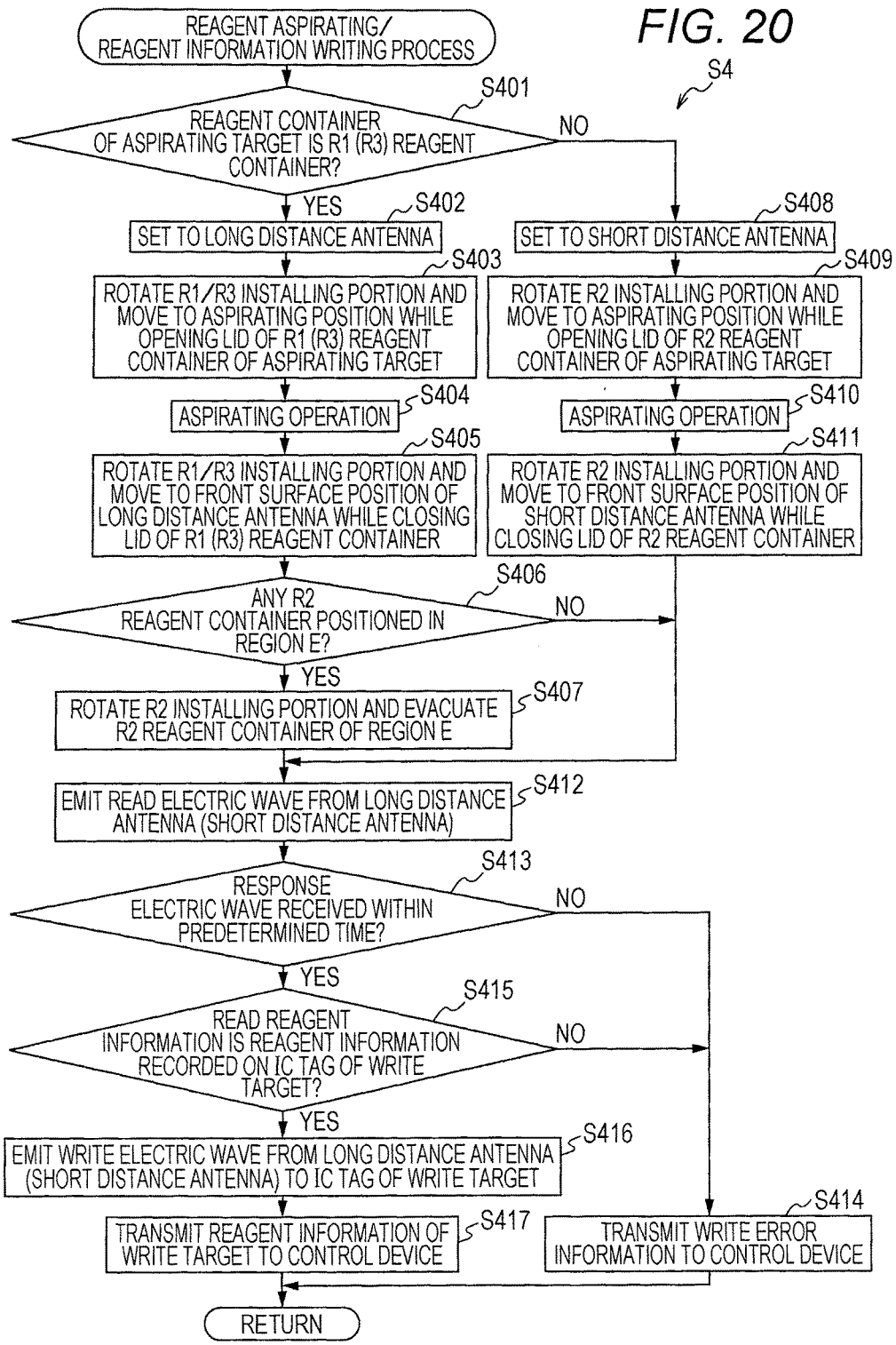
FIG. 20 is a flowchart showing the reagent aspirating/reagent information writing process of the immune analyzer according to the first embodiment shown in FIG. 1.

The reagent aspirating/reagent information writing process of the immune analyzer 1 according to the first embodiment of the present invention shown in step S4 of FIG. 18 will be described in detail with reference to FIG. 17 and FIG. 20.

First, in step S401, whether or not the reagent container of the target (aspirating target) to aspirate the reagent is the R1 reagent container 22 or the R3 reagent container 23 is determined by the CPU 2a. The reagent container of the aspirating target is transmitted to the CPU 2a through the CPU 4a based on the measurement conditions and the like input to the input unit 4c by the user.

If determined that the reagent container of the aspirating target is the R1 reagent container 22 or the R3 reagent container 23, the antenna that emits the read electric wave and the write electric wave is set to the long distance antenna 21 by the CPU 2a in step S402. Thereafter, in step S403, the R1/R3 installing portion 18 is rotated in the direction of the arrow C1 or the direction of the arrow C2 (see FIG. 17) so that the R1 reagent container 22 (R3 reagent container 23) of the aspirating target is positioned at the aspirating position at where the R1 reagent (R3 reagent) is aspirated by the R1 reagent dispensing arm 6 (R3 reagent dispensing arm 8) by the CPU 2a. In this case, the lid 22a of the R1 reagent container 22 (lid 23a of the R3 reagent container 23) is opened with the rotation of the R1/R3 installing portion 18.

In step S404, the R1 reagent (R3 reagent) is aspirated by the R1 reagent dispensing arm 6 (R3 reagent dispensing arm 8). Thereafter, in step S405, the R1/R3 installing portion 18 is rotated in the direction of the arrow C1 or the direction of the arrow C2 so that the IC tag 25 of the R1 reagent container 22 of the write target is positioned at a position opposing the long distance antenna 21 by the CPU 2a. In this case, the lid 22a of the R1 reagent container 22 (lid 23a of the R3 reagent container 23) is closed with the rotation of the R1/R3 installing portion 18.

In step S406, whether or not the R2 reagent container 24 is positioned in the region E (see FIG. 17) is determined by the CPU 2a. If determined that the R2 reagent container 24 is positioned in the region E, in step S407, the R2 installing portion 19 is rotated in the direction of the arrow D1 or the direction of the arrow D2 (see FIG. 17) so that the R2 reagent container 24 positioned in the region E is evacuated from the region E by the CPU 2a. The process then proceeds to step S412.

If determined that the reagent container of the aspirating target is the R2 reagent container 24 by the CPU 2a in step S401, the antenna for emitting the read electric wave and the write electric wave is set to the short antenna unit 20 in step S408. Thereafter, in step S409, the R2 installing portion 19 is rotated in the direction of the arrow D1 or the direction of the arrow D2 so that the R2 reagent container 24 of the aspirating target is positioned at the aspirating position at where the R2 reagent is aspirated by the R2 reagent dispensing arm 7 by the CPU 2a. In this case, the lid 24a of the R2 reagent container 24 is opened with the rotation of the R2 installing portion 19.

In step S410, the R2 reagent is aspirated by the R2 reagent dispensing arm 7. Thereafter, in step S411, the R2 installing portion 19 is rotated in the direction of the arrow D1 or the direction of the arrow D2 so that the IC tag 26 of the R2 reagent container 24 of the write target is positioned at a position opposing the short distance antenna 20 by the CPU 2a. In this case, the lid 24a of the R2 reagent container 24 is closed with the rotation of the R2 installing portion 19. The process then proceeds to step S412.

In step S412, the long distance read electric wave in the range B (short distance read electric wave in the range A) is emitted from the long distance antenna 21 (short distance antenna 20) to the IC tag 25 of the R1 reagent container 22 (IC tag 26 of the R2 reagent container 24) of the write target by the control of the CPU 2a. Thereafter, in step S413, whether or not the long distance antenna 21 (short distance antenna 20) received the response electric wave within a predetermined time is determined by the CPU 2a. If determined that the long distance antenna 21 (short distance antenna 20) did not receive the response electric wave within a predetermined time, the read error information is transmitted to the control device 4 by the CPU 2a in step S414, and a notification that the write of the reagent information to the IC tag of the write target is not carried out is displayed on the display unit 4b of the control device 4. The reagent aspirating/reagent information writing process is then terminated, and the process proceeds to step S5 shown in FIG. 18.

If determined that the long distance antenna 21 (short distance antenna 20) received the response electric wave within a predetermined time in step S413, whether or not the reagent information contained in the response electric wave received by the long distance antenna 21 (short distance antenna 20) is the reagent information recorded in the IC tag of the write target is determined by the CPU 2a in step S415. In this case, the CPU 2a determines whether or not the reagent information contained in the response electric wave is the reagent information recorded on the IC tag of the write target based on the reagent type (type specifying information) obtained from the response electric wave. If determined that the reagent information contained in the response electric wave is not the reagent information recorded on the IC tag of the write target, the process proceeds to step S414.

If determined that the reagent information contained in the response electric wave is the reagent information recorded on the IC tag of the write target, the long distance write electric wave (short distance write electric wave) including the remaining amount information and the like of the reagent is transmitted from the long distance antenna 21 (short distance antenna 20) to the IC tag 25 of the R1 reagent container 22 (IC tag 26 of the R2 reagent container 24) of the write target in step S416. In step S417, the information same as the reagent information written on the IC tag is transmitted from the CPU 2a to the control device 4, and then the reagent aspirating/reagent information writing process is terminated, and the process proceeds to step S5 shown in FIG. 18. In the control device 4, the reagent information of the storage unit 4d is updated based on the reagent information transmitted from the CPU 2a.

In the first embodiment, the substantially circular ring shaped R1/R3 installing portion 18 is arranged on the inner peripheral side of the substantially circular ring shaped R2 installing portion 19, and the short distance antenna 20 and the long distance antenna 21 are both arranged on the outer peripheral side of the R2 installing portion 19 when seen in plan view. Thus, only the region on the outer peripheral side of the R2 installing portion 19 needs to be ensured to arrange the short distance antenna 20 and the long distance antenna 21, and the region on the inner peripheral side of the R1/R3 installing portion 18 does not need to be ensured, and hence, the region on the inner peripheral side of the R1/R3 installing portion 18 can be reduced. As a result, the main body of the immune analyzer 1 can be suppressed from enlarging by such amount. The reagent information is suppressed from being mistakenly read from the IC tag 26 when reading the reagent information from the IC tag 25 by arranging both the short distance antenna 20 and the long distance antenna 21 on the outer peripheral side of the R2 installing portion 19.

In the first embodiment, the reaching range (range A) of the electric wave emitted when reading the reagent information recorded on the IC tag 26 of the R2 reagent container 24 installed in the R2 installing portion 19 is smaller than the reaching range (range B) of the electric wave emitted when reading the reagent information recorded on the IC tag 25 of the R1 reagent container 22 installed in the R1/R3 installing portion 18. Therefore, the reagent information recorded on a plurality of surrounding IC tags 26 and IC tags 25 adjacent to the IC tag 26 of the read target can be suppressed from being mistakenly read when reading the reagent information recorded on the IC tag 26.

In the first embodiment, the IC tags 25 and 26 can be simultaneously read by arranging the short distance antenna 20 and the long distance antenna 21, and hence the reagent information of a greater number of IC tags 25 and 26 can be read in a short period of time compared to when reading the IC tag with only one antenna.

Furthermore, in the first embodiment, whether or not the reagent information contained in the response electric wave received by the short distance antenna 20 and the long distance antenna 21 is the reagent information of the read target is determined based on the reagent type (type specifying information) contained in the response electric wave by the CPU 2a. Thus, the response electric wave from the IC tag 25 or 26 that is not the read target can be suppressed from being mistakenly used as the response electric wave of the read target.

In the first embodiment, the R1 reagent container 22 accommodates the R1 reagent, and the R2 reagent corner 24 accommodates the reagent of R2 type. Thus, only one type (R1 type) of reagent is accommodated in each R1 reagent container 22 held at the R1/R3 installing portion 18, and only one type (R2 type) of reagent is accommodated in each R2 reagent container 24 held at the R2 installing portion 19.

The CPU 2a then can easily determine which reagent information, the IC tag 25 or 26, is read.

In the first embodiment, twenty-five R1 reagent containers 22 are arranged at equal angle (about 14.4 degrees) in the substantially circular ring shaped R1/R3 installing portion 18, and twenty-five R2 reagent containers 24 are arranged at equal angle (about 14.4 degrees) in the substantially circular ring shaped R2 installing portion 19 arranged on the outer peripheral side of the R1/R3 installing portion 18. The interval between the adjacent reagent containers thus reliably becomes larger in the R2 installing portion 19 than in the R1/R3 installing portion 18. Therefore, the reagent information is suppressed from being mistakenly read from the IC tag 26 when reading the reagent information from the IC tag 25.

In the first embodiment, the R2 reagent container 24 positioned in the region E is evacuated from the region E when the long distance antenna 21 emits the long distance read electric wave in the range B. Therefore, the IC tag 25 of the R1 reagent container 22 can be suppressed from being difficult to be read due to the positioning of the R2 reagent container 24 in the region E.

In the first embodiment, the reaching range of the electric wave from the long distance antenna 21 can be limited to the range only the IC tag 25 of the R1 reagent container 22 of the read target is positioned by arranging the metal plate 21e for limiting the reaching range of the electric wave from the long distance antenna 21. Thus, the IC tags 25 and 26 that are not the read target can be suppressed from being mistakenly read by the long distance antenna 21.

In the first embodiment, the reaching range of the electric wave from the short distance antenna 20 can be limited to the range only the IC tag 26 of the R2 reagent container 24 of the read target is positioned by arranging the metal plate 20e for limiting the reaching range of the electric wave from the short distance antenna 20. Thus, the IC tags 25 and 26 that are not the read target can be suppressed from being mistakenly read by the short distance antenna 20.

(Second Embodiment)

A second embodiment will now be described with reference to FIG. 21 to FIG. 26. In an immune analyzer 301 according to the second embodiment, an example in which one antenna 321 is arranged in a reagent installing unit 316 of a measurement mechanism section 302 will be described as opposed to the first embodiment in which two antennas of the short distance antenna 20 and the long distance antenna 21 are arranged in the reagent installing unit 16 of the measurement mechanism section 2.

The configuration of the immune analyzer 301 according to the second embodiment of the present invention will be described first with reference to FIGS. 21 to 24.

Figure 21:
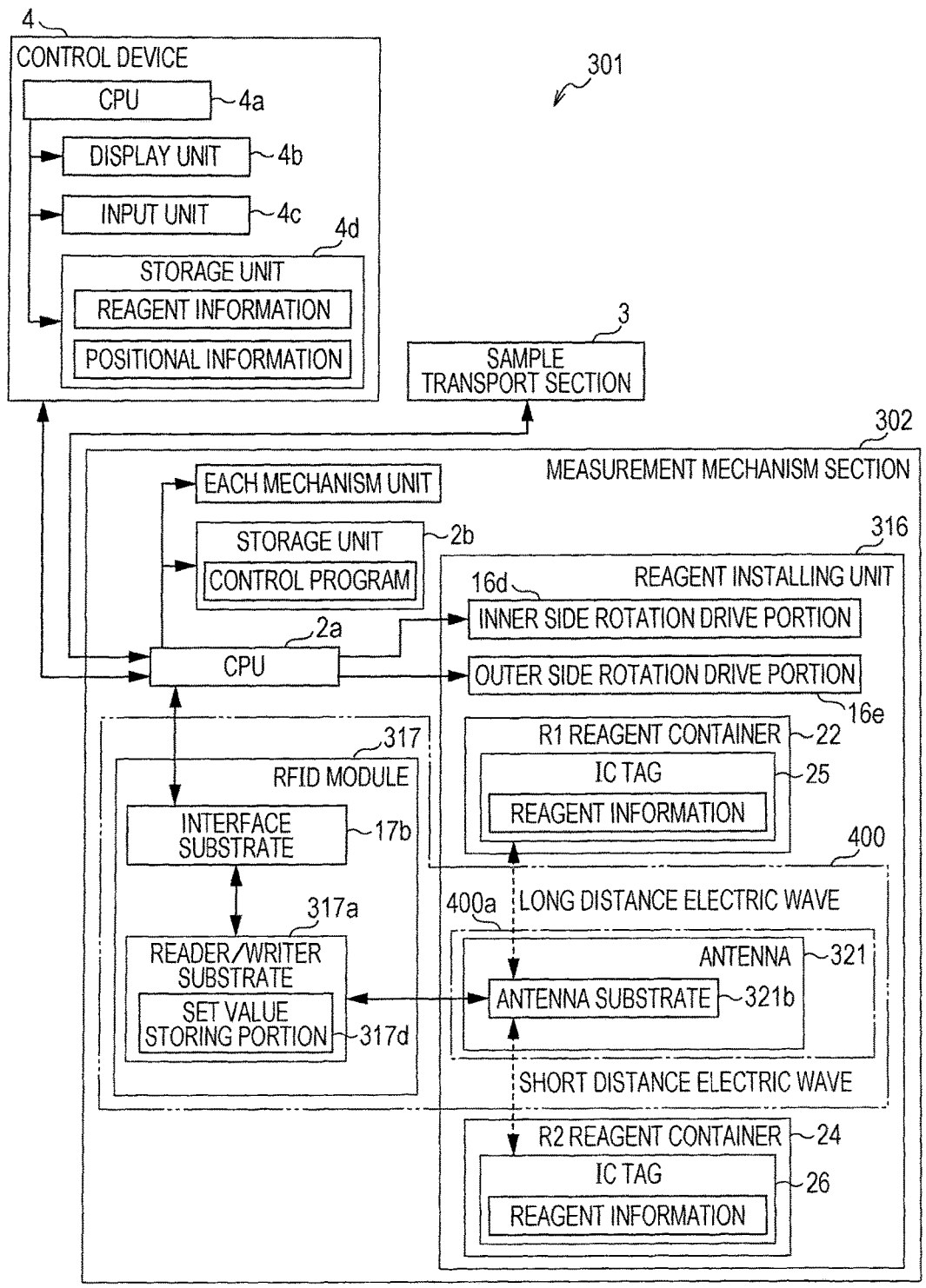
FIG. 21 is a block diagram for describing a configuration of an immune analyzer according to a second embodiment of the present invention.
Figure 22:
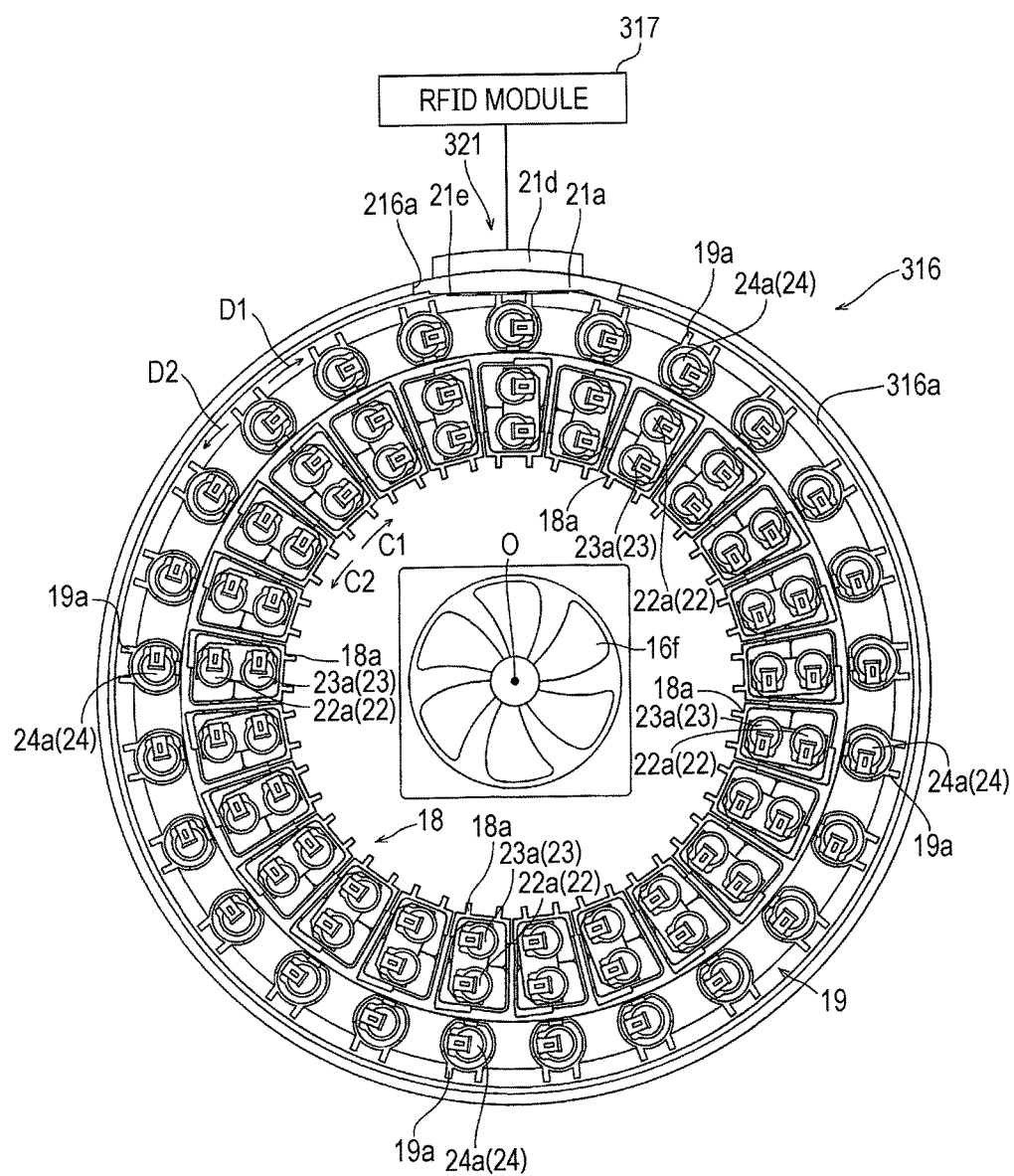
FIG. 22 is a plan view showing the interior of the reagent installing unit of the immune analyzer according to the second embodiment shown in FIG. 21.

In the second embodiment, one antenna 321 is arranged in the reagent installing unit 316, as shown in FIG. 21. As shown in FIG. 22, the antenna 321 is attached to a housing 316a by having a stopping portion 21a stop at the cutout 216a of the housing 316a of the reagent installing unit 316. The housing 316a of the second embodiment does not include the cutout 116a of the first embodiment.

Figure 23:
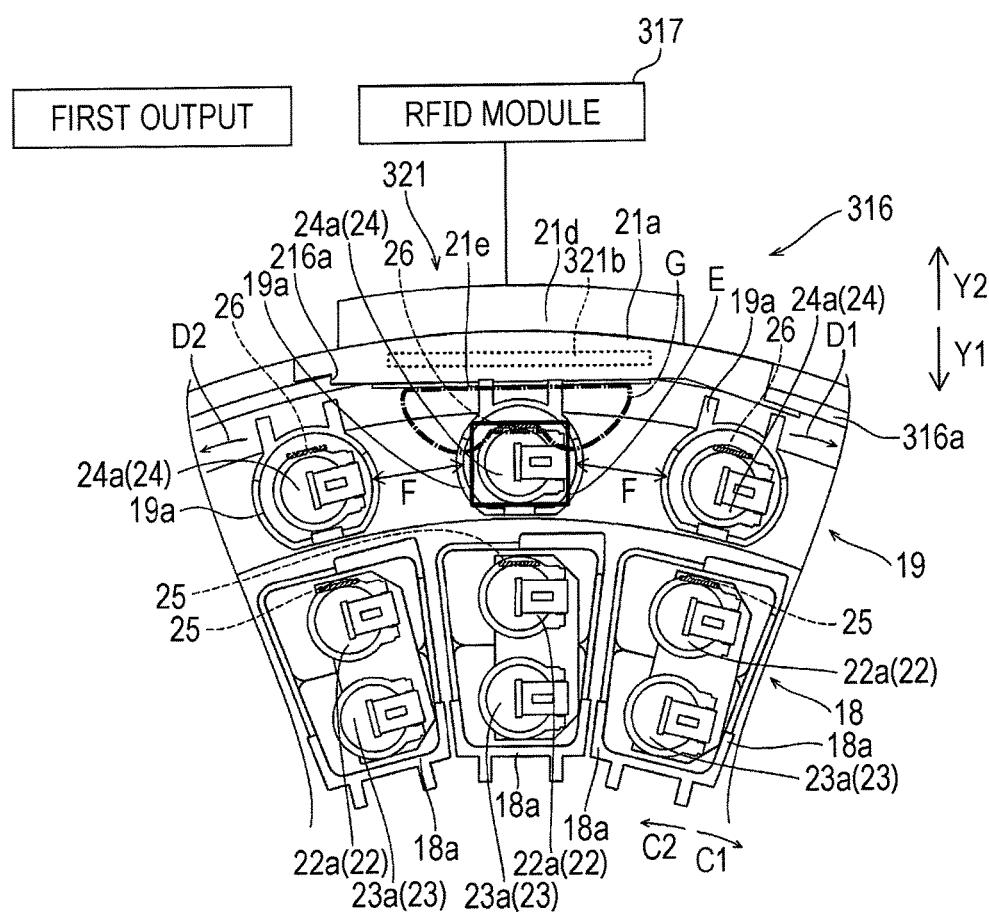
FIG. 23 is an enlarged plan view showing a state of when reading an IC tag of an R2 reagent container of the reagent installing unit according to the second embodiment shown in FIG. 21.
Figure 24:
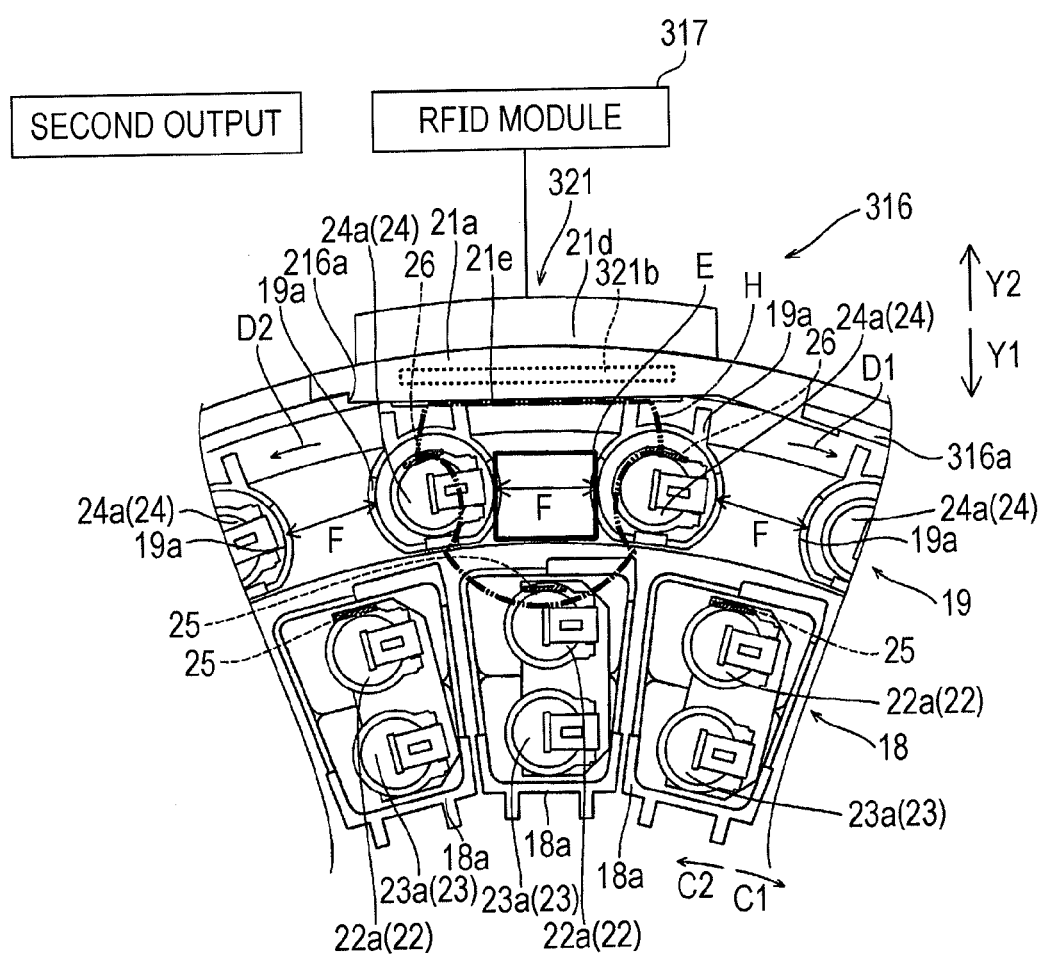
FIG. 24 is an enlarged plan view showing a state of when reading an IC tag of an R1 reagent container of the reagent installing unit according to the second embodiment shown in FIG. 21.

As shown in FIG. 21, the antenna 321 includes an antenna substrate 321b. As shown in FIG. 23 and FIG. 24, the antenna substrate 321b is configured such that the read electric wave and the write electric wave can be emitted toward the inner side of the reagent installing unit 316 (center O side of FIG. 22 (direction of arrow Y1)), and is configured to receive the response electric wave emitted from the IC tags 25 and 26 in response to the read electric wave. Other configurations of the antenna 321 are similar to the configurations of the long distance antenna 21 of the first embodiment.

In the second embodiment, the RFID module 317 includes a reader/writer substrate 317a, as shown in FIG. 21. The reader/writer substrate 317a includes a set value storing portion 317d for storing a set value of the transmission output to the antenna substrate 321b, where such set value is set by the CPU 2a. The transmission output from the reader/writer substrate 317a to the antenna substrate 321b is switched, and two types of read electric wave, the short distance read electric wave in the range G (chain dashed line in FIG. 23) where the read range is small and the long distance read electric wave in the range H (chain double dashed line in FIG. 24) where the read range is large, can be emitted from the antenna 321 by having the CPU 2a change the set value of the set value storing portion 317d. Similarly, two types of write electric wave, short distance write electric wave in the range G where the write range is small and the long distance write electric wave in the range H where the write range is large can be emitted from the antenna 321 by having the CPU 2a change the set value of the set value storing portion 317d. Thus, the read range of the read electric wave and the write range of write electric wave emitted from the antenna 321 can be switched to the range G of FIG. 23 (thick chain dashed line) and the range H of FIG. 24 (thick chain double dashed line) having a larger range than the range G by the CPU 2a and the reader/writer substrate 317a.

In the second embodiment, only one antenna 321 is arranged, and thus the antenna switching substrate 17c of the first embodiment for switching the antenna is unnecessary. As shown in FIG. 21, the antenna substrate 321b of the antenna 321 is directly connected to the reader/writer substrate 317a.

As shown in FIG. 21, in the second embodiment, the RFID module 317 and the antenna 321 configure a reagent information reading unit 400 for reading the reagent information recorded on the IC tags (IC tags 25 and 26). The antenna 321 functions as an electric wave emitting portion 400a for emitting electric wave to the IC tags.

Other configurations of the second embodiment are similar to those of the first embodiment.

The measurement operation of the immune analyzer 301 according to the second embodiment will now be described. The processes other than the reagent information reading process and the reagent aspirating/reagent information writing process are similar to those of the first embodiment shown in FIG. 18.

Figure 25:
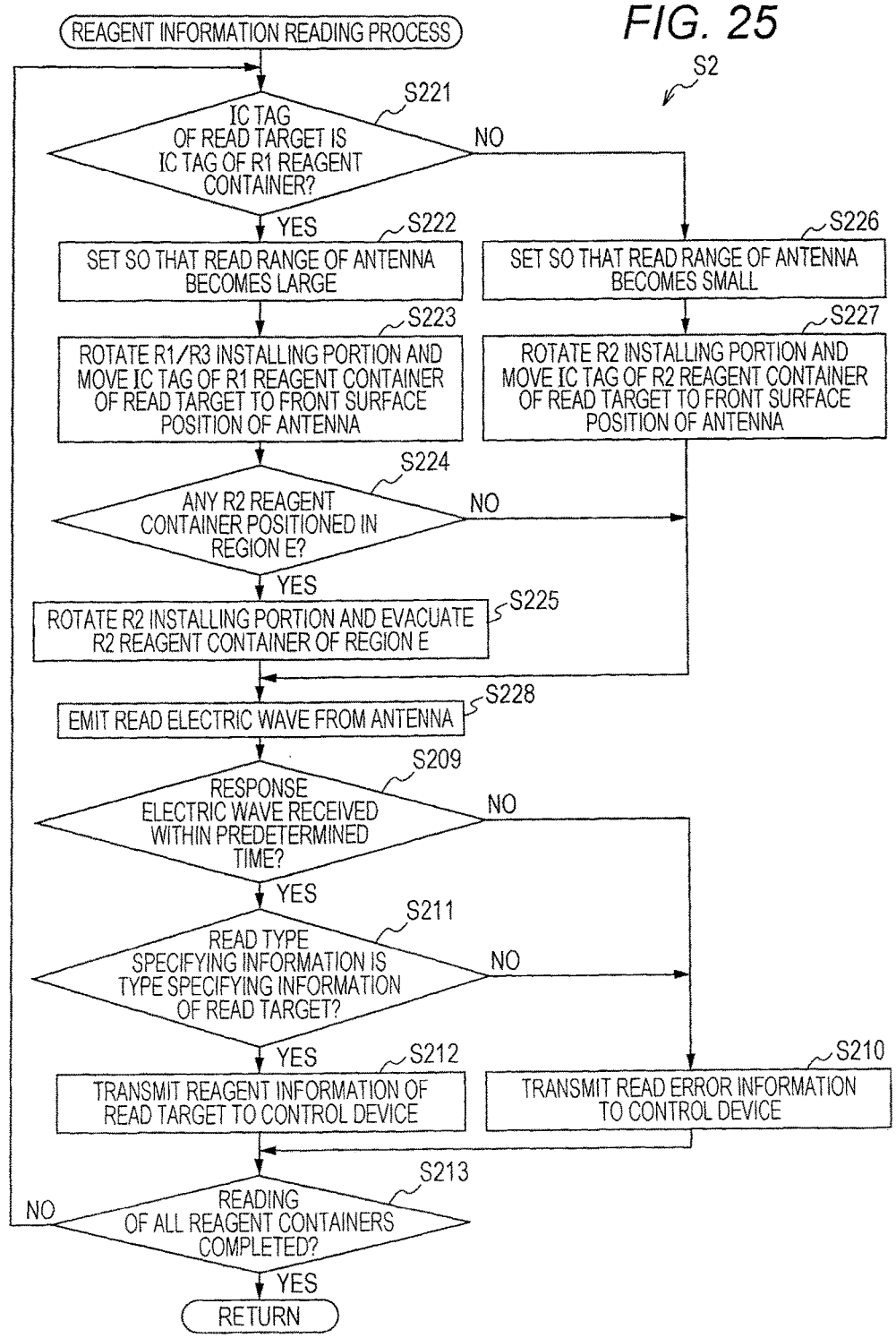
FIG. 25 is a flowchart showing the reagent information reading process of the immune analyzer according to the second embodiment shown in FIG. 21.

The reagent information reading process of the immune analyzer 301 according to the second embodiment of the present invention will be described in detail with reference to FIG. 23 to FIG. 25.

First, in step S221, whether or not the IC tag of the read target is the IC tag 25 of the R1 reagent container 22 is determined by the CPU 2a.

If determined that the IC tag of the read target is the IC tag 25 of the R1 reagent container 22, the transmission output from the reader/writer substrate 317a to the antenna substrate 321b is set so that the antenna 321 emits the long distance read electric wave in the range H (see FIG. 24) by the CPU 2a in step S222. In other words, the set value of the set value storing portion 317d of the reader/writer substrate 317a is set by the CPU 2a so that the read range of the antenna 321 becomes large. Thereafter, in step S223, the R1/R3 installing portion 18 is rotated in the direction of the arrow C1 or the direction of the arrow C2 (see FIG. 24) so that the IC tag 25 of the read target is positioned at the position opposing the antenna 321 by the CPU 2a.

In step S224, whether or not the R2 reagent container 24 is positioned in the region E (see FIG. 23) is determined by the CPU 2a. Thus, if determined that the R2 reagent container 24 is positioned in the region E, in step S225, the R2 installing portion 19 is rotated in the direction of the arrow D1 or the direction of the arrow D2 (see FIG. 23) so that the R2 reagent container 24 positioned in the region E is evacuated from the region E by the CPU 2a. The process then proceeds to step S228. If determined that none of the R2 reagent containers 24 is positioned in the region E in step S224, the process proceeds to step S228.

If determined that the IC tag of the read target is the IC tag 26 of the R2 reagent container 24 in step S221, the transmission output from the reader/writer substrate 317a to the antenna substrate 321b is set so that the antenna 321 emits the short distance read electric wave in the range G (see FIG. 23) by the CPU 2a in step S226. In other words, the set value of the set value storing portion 317d of the reader/writer substrate 317a is set by the CPU 2a so that the read range of the antenna 321 becomes small. Thereafter, in step S227, the R2 installing portion 19 is rotated in the direction of the arrow D1 or the direction of the arrow D2 so that the IC tag 26 of the read target is positioned at a position opposing the antenna 321 by the CPU 2a. The process then proceeds to step S228.

Figure 19:
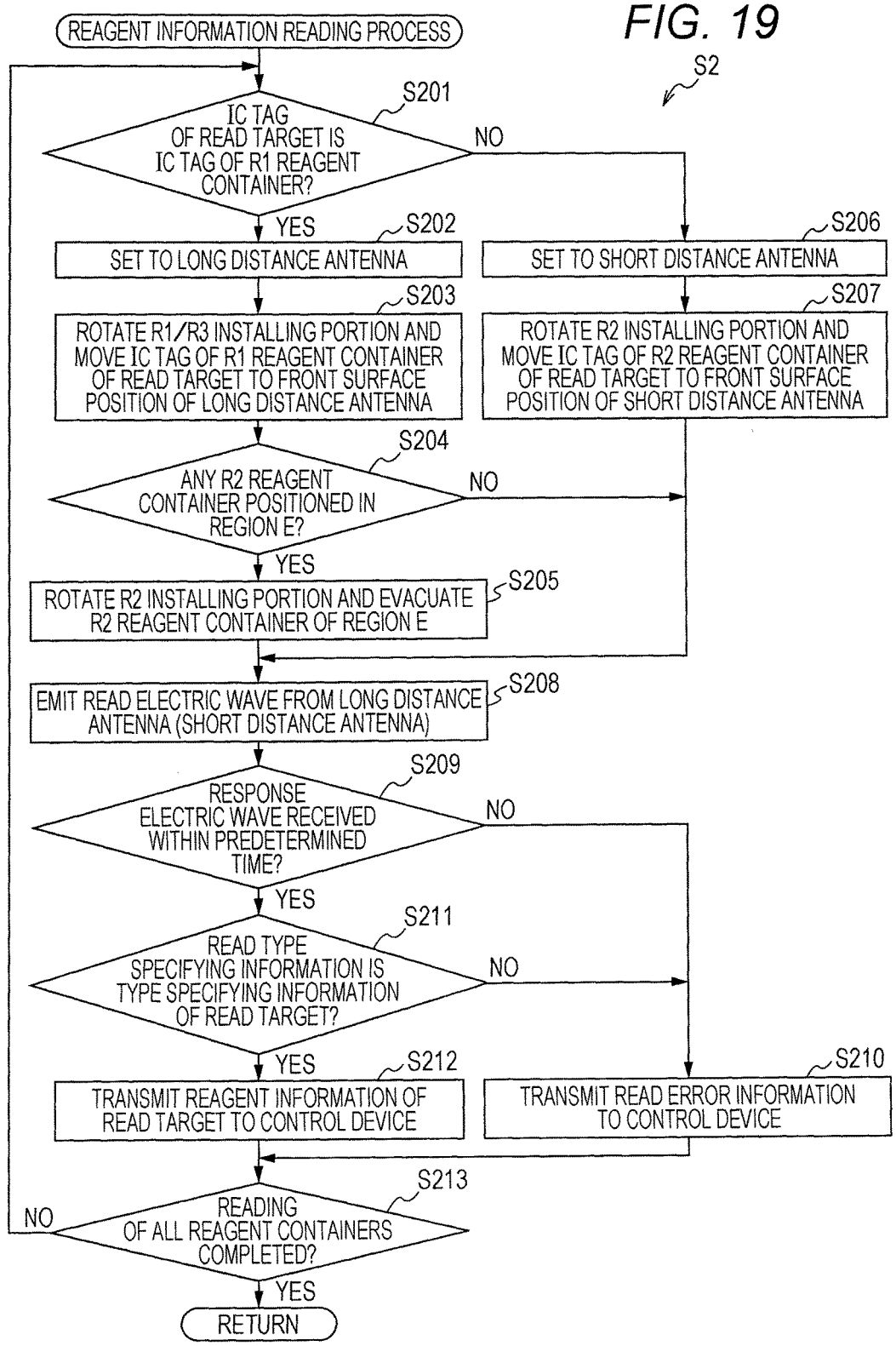
FIG. 19 is a flowchart showing the reagent information reading process of the immune analyzer according to the first embodiment shown in FIG. 1.

In step S228, the long distance read electric wave in the range H (short distance read electric wave in the range G) is emitted from the antenna 321 to the IC tag 25 of the R1 reagent container 22 (IC tag 26 of the R2 reagent container 24) of the read target by the CPU 2a. Thereafter, the processes similar to steps S209 to S213 of the first embodiment shown in FIG. 19 are executed, and the process proceeds to step S3 shown in FIG. 18.

Figure 26:
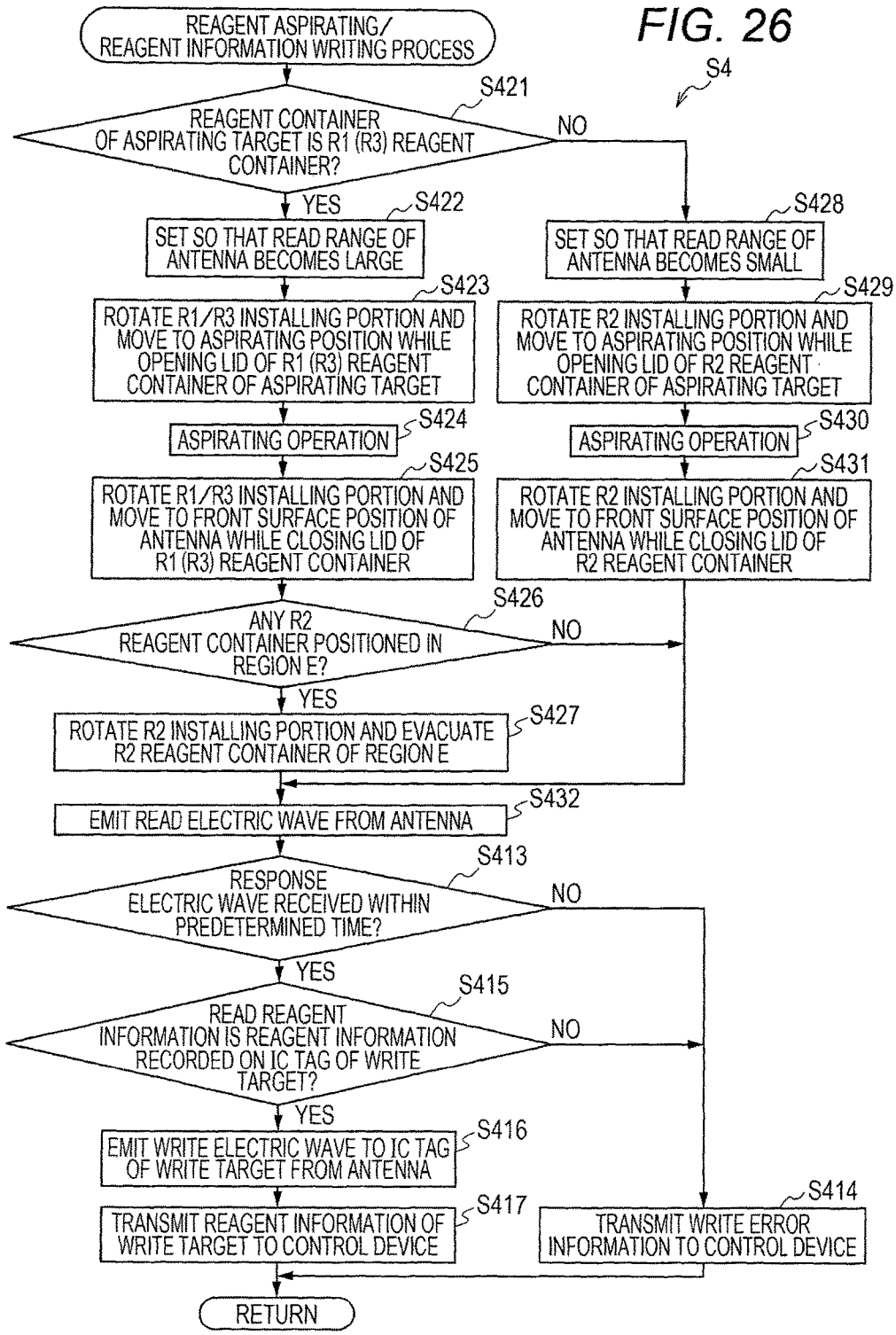
FIG. 26 is a flowchart showing the reagent aspirating/reagent information writing process of the immune analyzer according to the second embodiment shown in FIG. 21.

The reagent aspirating/reagent information writing process of the immune analyzer 301 according to the second embodiment of the present invention will be described in detail with reference to FIG. 23, FIG. 24, and FIG. 26.

Similar to the first embodiment, whether or not the reagent container of the target (aspirating target) to aspirate the reagent is the R1 reagent container 22 or the R3 reagent container 23 is determined by the CPU 2a in step S421.

If determined that the reagent container of the aspirating target is the R1 reagent container 22 or the R3 reagent container 23, the antenna 321 is set to emit the long distance read electric wave and the long distance write electric wave in the range H (see FIG. 24) by the CPU 2a in step S422. In other words, it is set such that the read range and the write range of the antenna 321 become large. Thereafter, in step S423, the R1/R3 installing portion 18 is rotated in the direction of the arrow C1 or the direction of the arrow C2 (see FIG. 24) so that the R1 reagent container 22 (R3 reagent container 23) of the aspirating target is positioned at the aspirating position by the CPU 2a. In this case, the lid 22a of the R1 reagent container 22 (lid 23a of the R3 reagent container 23) is opened with the rotation of the R1/R3 installing portion 18.

In step S424, the R1 reagent (R3 reagent) is aspirated. Thereafter, in step S425, the R1/R3 installing portion 18 is rotated in the direction of the arrow C1 or the direction of the arrow C2 (see FIG. 24) so that the IC tag 25 of the R1 reagent container 22 of the write target is positioned at a position opposing the antenna 321 by the CPU 2a. In this case, the lid 22a of the R1 reagent container 22 (lid 23a of the R3 reagent container 23) is closed with the rotation of the R1/R3 installing portion 18.

In step S426, whether or not the R2 reagent container 24 is positioned in the region E (see FIG. 23) is determined by the CPU 2a. Thus, if determined that the R2 reagent container 24 is positioned in the region E, in step S427, the R2 installing portion 19 is rotated in the direction of the arrow D1 or the direction of the arrow D2 (see FIG. 24) so that the R2 reagent container 24 positioned in the region E is evacuated from the region E by the CPU 2a. The process then proceeds to step S432.

If determined that the reagent container of the aspirating target is the R2 reagent container 24 in step S421, the antenna 321 is set to emit the short distance read electric wave and the short distance write electric wave in the range G (see FIG. 23) by the CPU 2a in step S428. In other words, it is set such that the read range and the write range of the antenna 321 become small. Thereafter, in step S429, the R2 installing portion 19 is rotated in the direction of the arrow D1 or the direction of the arrow D2 so that the R2 reagent container 24 of the aspirating target is positioned at the aspirating position by the CPU 2a. In this case, the lid 24a of the R2 reagent container 24 is opened with the rotation of the R2 installing portion 19.

In step S430, the R2 reagent is aspirated. Thereafter, in step S431, the R2 installing portion 19 is rotated in the direction of the arrow D1 or the direction of the arrow D2 so that the IC tag 26 of the R2 reagent container 24 of the write target is positioned at a position opposing the antenna 321 by the CPU 2a. In this case, the lid 24a of the R2 reagent container 24 is closed with the rotation of the R2 installing portion 19. The process then proceeds to step S432.

In step S432, the long distance read electric wave in the range H (short distance read electric wave in the range G) is emitted from the antenna 321 to the IC tag 25 of the R1 reagent container 22 (IC tag 26 of the R2 reagent container 24) of the write target by the control of the CPU 2a. Thereafter, the processes similar to steps S413 to S417 of the first embodiment shown in FIG. 20 are executed, and the process proceeds to step S5 shown in FIG. 18.

In the second embodiment, the read range of the read electric wave and the write range of the write electric wave emitted from one antenna 321 can be switched to the range G and the range H greater than the range G by switching the transmission output from the reader/writer substrate 317a to the antenna substrate 321b. Therefore, the antenna for reading the IC tag 25 of the R1 reagent container 22 and the antenna for reading the IC tag 26 of the R2 reagent container 24 do not need to be individually arranged, and hence the number of components can be suppressed from increasing.

Other effects of the second embodiment are similar to those of the first embodiment.

The embodiments disclosed herein are illustrative and should not be construed as being restrictive in all aspects. The scope of the invention is defined by the scope of the claims rather than by the description of the embodiments, and meaning equivalent to the claims and all modifications within the scope is encompassed herein.

For instance, an example of applying the sample analyzer of the present invention to the immune analyzer 1 (301) has been described in the first and second embodiments, but the present invention is not limited thereto. The present invention can be applied to any apparatus including the reagent information reading unit used to read the reagent information of the electronic tag, and is also applicable to a blood coagulation analyzer, a urine specimen measurement device, a gene amplification detection device and the like other than the immune analyzer.

Examples have been described, in which two antennas, the short distance antenna 20 and the long distance antenna 21 are both arranged at the outer peripheral side of the R2 installing portion 19 in the first embodiment, and in which one antenna 321 is arranged at the outer peripheral side of the R2 installing portion 19 in the second embodiment, but the present invention is not limited thereto. In the present invention, three or more antennas (electric wave emitting portion) may be arranged at the outer peripheral side of the R2 installing portion.

An example in which the short distance antenna 20 and the long distance antenna 21 (antenna 321) are both arranged at the outer peripheral side of the R2 installing portion 19 has been described in the first and second embodiments, but the present invention is not limited thereto. In the present invention, the antenna (electric wave emitting portion) may be arranged at the inner peripheral side of the R1 installing portion. In this case, the device main body can be suppressed from becoming large as the region on the outer peripheral side of the R2 installing portion does not need to be ensured for the electric wave emitting portion.

An example in which the R1/R3 installing portion 18 and the R2 installing portion 19 are arranged in a substantially circular ring shape has been described in the first and second embodiments, but the present invention is not limited thereto. For instance, the R1/R3 installing portion and the R2 installing portion may be arranged to extend linearly in a predetermined direction parallel to each other.

An example in which the short distance antenna 20 and the long distance antenna 21 (antenna 321) are configured to be able to emit the read electric wave and the write electric wave has been described in the first and second embodiments, but the present invention is not limited thereto. In the present invention, the antenna (electric wave emitting portion) may be configured to emit only the read electric wave.

An example in which the R1 reagent container 22 attached with the IC tag 25, the R2 reagent container 24 attached with the IC tag 26, and the R3 reagent container 23 not attached with the IC tag are arranged has been described in the first and second embodiments, but the present invention is not limited thereto. In the present invention, only the reagent container attached with the IC tag may be arranged without including the reagent container not attached with the IC tag.

An example in which the reagent information of the R1 reagent of the R1 reagent container 22 and the reagent information of the R3 reagent of the R3 reagent container 23 held at the R1/R3 holding member 18*a* common with the R1 reagent container 22 are recorded in the IC tag 25 has been described in the first and second embodiments, but the present invention is not limited thereto. In the present invention, three or more reagent information may be recorded on one IC tag.

An example in which twenty-five R1 reagent containers 22, twenty-five R3 reagent containers 23, and twenty-five R2 reagent containers 24 are arranged has been described in the first and second embodiments, but the present invention is not limited thereto. In the present invention, the number of the R1 reagent container, the R3 reagent container, and the R2 reagent container may be differed. The number of R1 reagent container (R3 reagent container, R2 reagent container) may be other than twenty-five. For instance, only one of each of the R1 reagent container, the R3 reagent container, and the R2 reagent container may be arranged.

An example in which two columns of reagent container holding units (R1/R3 installing portion 18 and R2 installing portion 19) are arranged has been described in the first and second embodiments, but three or more columns of reagent container holding units may be arranged.

An example in which the R1/R3 installing portion 18 and the R2 installing portion 19 are respectively rotated by the inner side rotation drive portion 16*d* and the outer side rotation drive portion 16*e* has been described in the first and second embodiments, but the present invention is not limited thereto. In the present invention, the R1/R3 installing portion and the R2 installing portion may be configured so as not to rotate, and the electric wave emitting portion may be rotated by arranging a drive portion for rotating the antenna (electric wave emitting portion). In this case, the gap between the adjacent R2 containers is preferably positioned in a region where the R1 reagent container of the R1/R3 installing portion and the electric wave emitting portion face each other.

An example of switching the read range of the read electric wave and the write range of the write electric wave emitted from the antenna 321 by switching the transmission output from the reader/writer substrate 317*a* to the antenna substrate 321*b* has been described in the second embodiment, but the present invention is not limited thereto. For instance, the read range of the read electric wave and the write range of the write electric wave may be switched by configuring such that the shape and the size of the cutout of the metal plate (limiting member) can be appropriately adjusted by the CPU.

As shown in FIG. 4 and FIG. 5, one antenna 18 is attached to the housing 16*a* of the reagent installing unit 16 in the present embodiment. Specifically, as shown in FIG. 4 to FIG. 7, the housing 16*a* includes a cutout 116*a* formed by cutting out one part of the side wall along the vertical direction (see FIG. 4). The cutout 116*a* is configured so as to stop the resin stopping portion 18*a* of the antenna 18. In other words, the antenna 18 is fixed to the reagent installing unit 16.

As shown in FIG. 8 and FIG. 9, the antenna 18 includes an antenna substrate 18*b*, a substrate attachment portion 18*c* interiorly fixed with the antenna substrate 18*b*, a lid member 18*d* for covering the antenna substrate 18*b* from the outer side (side in the direction of the arrow X2), and a metal plate 18*e* attached to the surface on the side opposite to (side in the direction of the arrow X1) the antenna substrate 18*b* of the substrate attachment portion 18*c* in addition to the stopping portion 18*a*.

As shown in FIG. 10, the antenna substrate 18*b* is formed with a coil-shaped antenna wiring 180*b* on the surface (see FIG. 9) on the side in the direction of the arrow X1 of the plate-shaped substrate, so that electric wave can be transmitted and received through the coil-shaped antenna wiring 180*b*. As shown in FIG. 6 and FIG. 7, the antenna substrate 18*b* is arranged inside the substrate attachment portion 18*c* such that the surface on the side in the direction of the arrow X1 of the antenna substrate 18*b* faces the center O (see FIG. 5) of the housing 16*a*.

The antenna substrate 18*b* is configured such that the read electric wave and the write electric wave can be emitted toward the inner side of the reagent installing unit 16 (center O side of FIG. 5 (direction of arrow X1)), and is configured to receive the response electric wave emitted from the IC tags 22 and 23, to be described later, in response to the read electric wave. The antenna substrate 18*b* is connected to the reader/writer substrate 17*a*, to be described later, of the RFID module 17.

The substrate attachment portion 18*c* and the lid member 18*d* are both made of resin capable of transmitting the electric wave. As shown in FIG. 9, the substrate attachment portion 18c and the lid member 18d are arranged to protect the antenna substrate 18b from dew condensation and the like, and hence the antenna substrate 18b is isolated from the outside by the substrate attachment portion 18c and the lid member 18d. The antenna substrate 18b is fixed to the substrate attachment portion 18c with a screw 18f and a nut 18g.

The metal plate 18e is made of aluminum plate material capable of absorbing electric wave (read electric wave, write electric wave, and response electric wave). As shown in FIG. 8, the metal plate 18e is fixed to the substrate attachment portion 18c with a screw 18h and a nut (not shown) so as to be arranged on the surface on the side of the direction indicated with the arrow X1 of the substrate attachment portion 18c. The metal plate 18e is formed with a substantially U-shaped cutout 18i. The antenna substrate 18b is configured to emit the electric wave towards the inner side of the reagent installing unit 16 (direction of the arrow X1) through the cutout 18i, and to absorb the electric wave of the antenna substrate 18b that does not pass through the cutout 18i with the metal plate 18e. In other words, the metal plate 18e limits the read range and the write range of the antenna 18 (antenna substrate 18b) by limiting the range of the electric wave emitted from the antenna substrate 18b and the range of the electric wave received by the antenna substrate 18b.

As shown in FIG. 5, the R1/R3 installing portion 161 formed to a substantially circular ring shape having substantially the same center as the center O of the housing 16a and the R2 installing portion 162 formed to a substantially circular ring shape having substantially the same center as the center O of the housing 16a are arranged inside the housing 16a in plan view. The R1/R3 installing portion 161 is arranged on the inner peripheral side (center O side) of the R2 installing portion 162, and the one antenna 18 is arranged on the outer peripheral side (side opposite to the center O) of the R2 installing portion 162 when seen in plan view.

The reagent installing unit 16 includes the inner side rotation drive portion 16d (see FIG. 3) for rotating the R1/R3 installing portion 161 in the direction of the arrow C1 and in the direction of the arrow C2 with the center O as the center of rotation, and the outer side rotation drive portion 16e (see FIG. 3) for rotating the R2 installing portion 162 in the direction of the arrow D1 and in the direction of the arrow D2 with the center O as the center of rotation. The inner side rotation drive portion 16d and the outer side rotation drive portion 16e are configured such that the drive is individually controlled by the CPU 2a. A peltier element (not shown) and a fan 16f for cooling the R1 reagent, the R2 reagent, and the R3 reagent are arranged at the bottom of the housing 16a. This cooling may cause dew condensation in the reagent installing unit 16.

As shown in FIG. 5, the R1/R3 installing portion 161 includes twenty-five R1/R3 holding members 161a, which are made of resin capable of transmitting the electric wave, arranged at an equal angle (about 14.4 degrees). Each R1/R3 holding member 161a holds the R1 reagent container 19 for accommodating the R1 reagent containing the capture antibody, and the R3 reagent container 20 for accommodating the R3 reagent containing the labeled body. The R1/R3 holding member 161a is configured such that the R1 reagent container 19 is held on the outer side (R2 installing portion 162 side) and the R3 reagent container 20 is held on the inner side (center O side).

The R2 installing portion 162 includes twenty-five R2 holding members 162a, which are made of resin capable of transmitting the electric wave, arranged at an equal angle (about 14.4 degrees). Each R2 holding member 162a holds the R2 reagent container 21 for accommodating the R2 reagent containing the magnetic particles. The R1 reagent container 19, the R3 reagent container 20, and the R2 reagent container 21 are configured so as to be installable and replaceable by the user.

As shown in FIG. 11, the R1 reagent container 19 is formed with a lid 19a that opens and closes when aspirating the R1 reagent, and a reagent accommodating portion 19b for accommodating the R1 reagent. As shown in FIG. 12, the R2 reagent container 21 is formed with a lid 21a that opens and closes when aspirating the R2 reagent, and a reagent accommodating portion 21b for accommodating the R2 reagent. As shown in FIG. 6 and FIG. 7, the R3 reagent container 20 and the R1 reagent container 19 have substantially a similar shape, and the R3 reagent container 20 is formed with a lid 20a that opens and closes when aspirating the R3 reagent, and a reagent accommodating portion (not shown) for accommodating the R3 reagent. The lids 19a and 20a are configured to open and close with the rotation of the R1/R3 installing portion 161, and the lid 21a is configured to open and close with the rotation of the R2 installing portion 162.

As shown in FIG. 11, an IC tag attachment portion 19c, to which the IC tag 22 is to be attached, is formed on the side surface arranged on the outer side (direction of arrow X2 in FIG. 6) of the reagent accommodating portion 19b of the R1 reagent container 19. As shown in FIG. 12, an IC tag attachment portion 21c, to where the IC tag 23 is to be attached, is formed on the side surface arranged on the outer side (direction of arrow X2 in FIG. 6) of the reagent accommodating portion 21b of the R2 reagent container 21. In other words, the IC tag 22 of the R1 reagent container 19 is attached to face the outer side (direction of the arrow X2) of the reagent installing unit 16 when arranged in the R1/R3 installing portion 161, as shown in FIG. 6 and FIG. 7. The IC tag 23 of the R2 reagent container 21 is attached to face the outer side of the reagent installing unit 16 when arranged in the R2 installing portion 162. An IC tag is not attached to the side surface of the R3 reagent container 20, as opposed to the R1 reagent container 19.

The IC tag 22 records the reagent information of the R1 reagent of the R1 reagent container 19, and the reagent information of the R3 reagent of the R3 reagent container 20 held in the R1/R3 holding member 161a common with the R1 reagent container 19. The IC tag 23 records the reagent information of the R2 reagent of the R2 reagent container 21.

As shown in FIG. 13, the IC tags 22 and 23 are configured to be able to store 128 bytes of information. Among the storage capacity of 128 bytes, 16 bytes are assigned for the unique ID region indicating the unique information, and 112 bytes are assigned for the user data region indicating the reagent information. The unique ID region is the region where the unique ID for individually identifying the IC tags 22 and 23 is recorded, and only read can be carried out. The user data region is the region where the user can freely write information. The user data region is set with a region (read only region) where only read is carried out and write is not carried out, and a region (writeable region) where both read and write are carried out.

The unique ID is used when the CPU 2a encrypts the reagent information. Thus, the reagent information cannot be decrypted if the unique ID is different even if the reagent information is duplicated to a different IC tag, and hence the reagent information and the reagent of the reagent container are suppressed from being wrongly corresponded.

The measurement item, the lot number, the serial number, the reagent type (type specifying information), the storage period, and the filled amount regarding the reagent container (R1 reagent container 19 or R2 reagent container 21) given the IC tag (IC tag 22 or 23) are recorded in the read only region, and the remaining amount and the expiration date for use are written in the writable region. The information is not written to the writable region of the IC tag 22 attached to the R1 reagent container 19 installed in the R1/R3 installing portion 161 for the first time, and the IC tag 23 attached to the R2 reagent container 21 installed in the R2 installing portion 162 for the first time.

The measurement item shows the measurement item performed with the reagent accommodated in the reagent container attached with the IC tag. The reagent type shows whether the reagent container attached with the IC tag is the R1 reagent container 19 or the R2 reagent container 21. The storage period shows the period the reagent can be stored. The filled amount shows the number of measurements that can be carried out with the reagent. The remaining amount shows the number of measurements that can be carried out with the reagent. The expiration date for use shows the date until the reagent can be used. The expiration date for use is set when the relevant reagent starts to be used.

In the present embodiment, the IC tags 22 and 23 are configured so that read and write are carried out at the front surface position (facing position) of the antenna 18, as shown in FIG. 6 and FIG. 7. In this case, the IC tags 22 and 23 are configured to emit the response electric wave containing the reagent information recorded on the IC tags 22 and 23 based on the read electric wave emitted from the antenna 18. The IC tags 22 and 23 are configured to rewrite the reagent information recorded on the IC tags 22 and 23 to the new reagent information contained in the write electric wave based on the write electric wave emitted from the antenna 18. The reagent information is recorded in the IC tags 22 and 23 in an encrypted state.

The IC tag 22 of the R1 reagent container 19 is configured so that read and write are carried out by the long distance read electric wave and the long distance write electric wave in the range B (thick double dashed line of FIG. 7) emitted from the antenna 18. The interval between the adjacent R1/R3 holding members 161a and the range B are set so that read and write are carried out on a specific IC tag 22, and read and write are not carried out on the other IC tag 22.

The IC tag 23 of the R2 reagent container 21 is configured so that read and write are carried out by the short distance read electric wave and the short distance write electric wave in the range A (thick chain dashed line of FIG. 6) smaller than the range B emitted from the antenna 18. The interval between the adjacent R2 holding members 162a and the range A are set so that read and write are carried out on a specific IC tag 23, and read and write are not carried out on the other IC tag 23.

In addition to the reagent information, the IC tags 22 and 23 are recorded with the unique ID unique to each IC tag 22 and 23. The unique ID is used when the CPU 2a encrypts the reagent information. Thus, the reagent information cannot be decrypted if the unique ID is different even if the reagent information is duplicated to a different IC tag, and hence the reagent information and the reagent of the reagent container are suppressed from being wrongly corresponded.

As shown in FIG. 3, respective reagent information of the twenty-five R1 reagent containers 19, the twenty-five R2 reagent containers 21, and the twenty-five R3 reagent containers 20 are individually stored in the storage unit 4d of the control device 4 apart from the IC tags 22 and 23. The storage unit 4d stores the respective initial position of the twenty-five R1 reagent containers 19, the twenty-five R3 reagent containers 20, and the twenty-five R2 reagent containers 21, and the rotation angle from the respective initial position of the R1/R3 installing portion 161 and the R2 installing portion 162 as positional information. The storage unit 4d thus stores the positional information and the reagent information of twenty-five R1 reagent containers 19, the twenty-five R3 reagent containers 20, and the twenty-five R2 reagent containers 21 in a corresponded state. The reagent information is stored in the storage unit 4d of the control device 4 in the decrypted state.

When the power supply (not shown) of the immune analyzer 1 is turned ON, the IC tags (IC tags 22 and 23) of all the reagent containers (R1 reagent container 19 and R2 reagent container 21) installed in the reagent installing unit 16 are read, and the positional information and the reagent information of each reagent container are acquired by the CPU 2a. If the reagent information is stored in the storage unit 4d, the CPU 4a of the control device 4 updates the reagent information stored in the storage unit 4d to the reagent information acquired from the IC tag when the power supply is turned ON. Thus, even if the R1 reagent container 19, the R3 reagent container 20, and the R2 reagent container 21 are respectively changed to a new R1 reagent container 19, R3 reagent container 20, and R2 reagent container 21 while the power supply of the immune analyzer 1 is turned OFF, the reagent information stored in the storage unit 4d of the control device 4 can be updated to the information of the reagent currently installed at the reagent installing unit 16.

As shown in FIG. 2, the RFID module 17 is arranged exterior to the reagent installing unit 16, and includes a reader/writer substrate 17a, and an interface substrate 17b for intermediating the reader/writer substrate 17a and the CPU 2a, as shown in FIG. 3.

The reader/writer substrate 17a is connected to the antenna 18, and is configured to emit the read electric wave and the write electric wave having the frequency band of about 13.56 MHz from the antenna 18 based on the instruction from the CPU 2a. The reader/writer substrate 17a is also configured to acquire the reagent information from the response electric wave emitted from the IC tags 22 and 23 in response to the read electric wave and received by the antenna 18, and to output the reagent information to the CPU 2a.

The reader/writer substrate 17a further includes a set value storing portion 17c for storing a set value of the transmission output to the antenna substrate 18b, where such set value is set by the CPU 2a. The transmission output from the reader/writer substrate 17a to the antenna substrate 18b is switched, and two types of read electric wave, the long distance read electric wave in the range B (thick chain double dashed line in FIG. 7) where the read range is large and the short distance read electric wave in the range A (thick chain dashed line in FIG. 6) where the read range is small, can be emitted from the antenna 18 by having the CPU 2a change the set value of the set value storing portion 17c. Similarly, two types of write electric wave, long distance write electric wave in the range B where the write range is large and the short distance write electric wave in the range A where the write range is small can be emitted from the antenna 18 by having the CPU 2a change the set value of the set value storing portion 17c. Thus, the read range of the read electric wave and the write range of write electric wave emitted from the antenna 18 can be switched to the range A of FIG. 6 (thick chain dashed line) and the range B of FIG. 7 (thick chain double dashed line) larger than the range A by the CPU 2a and the reader/writer substrate 17a.

The measurement operation of the immune analyzer 1 (measurement mechanism section 2) according to one embodiment of the present invention will now be described with reference to FIG. 3 and FIG. 14.

First, when the power supply of the measurement mechanism section 2 is turned ON, the CPU 2a of the measurement mechanism section 2 initializes the program in step S1 and executes an initialization process such as operation check of each unit of the measurement mechanism section 2.

Thereafter, the reagent information reading process is performed in step S2. The reagent information reading process will be described in detail later.

In step S3, whether or not a measurement instruction by the user is made is determined by the CPU 2a. The measurement instruction by the user is transmitted to the CPU 2a through the control device 4 (see FIG. 3). If determined that the measurement instruction by the user is not made, the process proceeds to step S6.

If determined that the measurement instruction by the user is made in step S3, the reagent aspirating/reagent information writing process is carried out by the CPU 2a in step S4. The reagent aspirating/reagent information writing process will be described in detail later.

Subsequently, the sample is measured in step S5. In step S6, whether or not the instruction to shut down by the user is made is determined by the CPU 2a. The process returns to step S3 if determined that the instruction of shutdown is not made. If determined that the instruction of shutdown is made, the shutdown of the measurement mechanism section 2 is carried out by the CPU 2a in step S7. The measurement operation of the measurement mechanism section 2 is terminated in such manner.

With reference to FIG. 6, FIG. 7, and FIG. 15, the reagent information reading process of the immune analyzer 1 according to one embodiment of the present invention shown in step S2 of FIG. 14 will be described in detail.

First, in step S201, whether or not the IC tag of the read target is the IC tag 22 of the R1 reagent container 19 is determined by the CPU 2a. If the IC tag of the read target is the IC tag 22 of the R1 reagent container 19, the process proceeds to step S202. If determined that the IC tag of the read target is the IC tag 23 of the R2 reagent container 21, the process proceeds to step S206.

In step S202, the transmission output from the reader/writer substrate 17a to the antenna substrate 18b is set by the CPU 2a so that the antenna 18 emits the long distance read electric wave in the range B (see FIG. 7). In other words, the set value of the set value storing portion 17c of the reader/writer substrate 17a is set by the CPU 2a so that the read range of the antenna 18 becomes large. Thereafter, in step S203, the R1/R3 installing portion 161 is rotated in the direction of the arrow C1 or the direction of the arrow C2 so that the IC tag 22 of the read target is positioned at the position (front surface position) opposing the antenna 18 by the CPU 2a.

In step S204, whether or not the R2 reagent container 21 is positioned in the region E (see FIG. 6) in the vicinity of the position opposing the antenna 18 is determined by the CPU 2a. In this case, whether or not the R2 reagent container 21 is positioned in the region E is determined based on the positional information of the R2 reagent container 21. If the R2 reagent container 21 is positioned in the region E, the read and write of the IC tag 22 may not be carried out even if the antenna 18 emits the long distance read electric wave and the long distance write electric wave in the range B (see FIG. 7) as the electric wave is absorbed by the R2 reagent accommodated in the R2 reagent container 21. Thus, if determined that the R2 reagent container 21 is positioned in the region E, in step S205, the R2 installing portion 162 is rotated in the direction of the arrow D1 or the direction of the arrow D2 so that the R2 reagent container 21 positioned in the region E is evacuated from the region E by the CPU 2a. Thus, as shown in FIG. 7, the gap F between the adjacent R2 reagent containers 21 and the IC tag 22 of the read target are arranged at the position opposing the antenna 18, and the IC tag 23 of the R2 reagent container 21 is arranged at the position not opposing the antenna 18. The process then proceeds to step S208. If determined that none of the R2 reagent containers 21 is positioned in the region E in step S204, the process proceeds to step S208.

If determined that the IC tag of the read target is the IC tag 23 of the R2 reagent container 21 in step S201, the transmission output from the reader/writer substrate 17a to the antenna substrate 18b is set so that the antenna 18 emits the short distance read electric wave in the range A (see FIG. 6) by the CPU 2a in step S206. In other words, the set value of the set value storing portion 17c of the reader/writer substrate 17a is set by the CPU 2a so that the read range of the antenna 18 becomes small. Thereafter, in step S207, the R2 installing portion 162 is rotated in the direction of the arrow D1 or the direction of the arrow D2 so that the IC tag 23 of the read target is positioned at a position opposing the antenna 18 by the CPU 2a. The process then proceeds to step S208.

In step S208, the long distance read electric wave in the range B or the short distance read electric wave in the range A is emitted from the antenna 18 to the IC tag 22 or the IC tag 23 of the read target by the control of the CPU 2a and the reader/writer substrate 17a.

Thereafter, in step S209, whether or not the response electric wave emitted from the IC tag 22 or 23 in correspondence to the long distance read electric wave or the short distance read electric wave is received within a predetermined time by the antenna 18 is determined by the CPU 2a. In other words, whether or not the reagent information acquired by the reader/writer substrate 17a of the RFID module 17 based on the response electric wave received from the antenna 18 is output to the CPU 2a within a predetermined time is determined by the CPU 2a. If determined that the antenna 18 did not receive the response electric wave within a predetermined time, the read error information is transmitted to the control device 4 by the CPU 2a in step S210. A notification that reading of the reagent information of the reagent container positioned at a predetermined position (reagent information of the reagent container of the read target) failed is displayed on the display unit 4b of the control device 4. The process then proceeds to step S213.

If determined that the antenna 18 received the response electric wave within a predetermined time in step S209, whether or not the reagent information contained in the response electric wave received by the antenna 18 is the reagent information of the read target is determined by the CPU 2a in step S211. In this case, the CPU 2a determines whether or not the reagent information contained in the response electric wave is the reagent information of the read target based on the reagent type (type specifying information) obtained from the response electric wave. If determined that the reagent information contained in the response electric wave is not the reagent information of the read target, the process proceeds to step S210.

If determined that the reagent information contained in the response electric wave is the reagent information of the read target, the reagent information of the read target contained in the response electric wave is transmitted from the CPU 2a to the control device 4 in step S212. When the antenna 18 receives a plurality of response electric waves, and the reagent information of the read target exists in the plurality of response electric waves, only the reagent information of the read target is transmitted to the control device 4. In the control device 4, the reagent information of the storage unit 4d is updated based on the reagent information of the read target received from the CPU 2a. The process then proceeds to step S213.

Finally, in step S213, whether or not the reading of all twenty-five IC tags 22 and twenty-five IC tags 23 is completed is determined by the CPU 2a. If determined that the reading is not completed, the process returns to step S201 and the reading of a new IC tag is carried out. If determined that all the reading is completed, the reagent information reading process is terminated, and the process proceeds to step S3 shown in FIG. 14.

With reference to FIG. 6, FIG. 7, and FIG. 16, the reagent aspirating/reagent information writing process of the immune analyzer 1 according to one embodiment of the present invention shown in step S4 of FIG. 14 will be described in detail.

First, in step S401, whether or not the reagent container of the target (aspirating target) to aspirate the reagent is the R1 reagent container 19 or the R3 reagent container 20 is determined by the CPU 2a. The reagent container of the aspirating target is transmitted to the CPU 2a through the CPU 4a based on the measurement conditions and the like input to the input unit 4c by the user.

If determined that the reagent container of the aspirating target is the R1 reagent container 19 or R3 reagent container 20, the R1/R3 installing portion 161 is rotated in the direction of the arrow C1 or the direction of the arrow C2 so that the R1 reagent container 19 (R3 reagent container 20) of the aspirating target is positioned at the aspirating position at where the R1 reagent (R3 reagent) is aspirated by the R1 reagent dispensing arm 6 (R3 reagent dispensing arm 8) by the CPU 2a in step S402. In this case, the lid 19a of the R1 reagent container 19 (lid 20a of the R3 reagent container 20) is opened with the rotation of the R1/R3 installing portion 161.

In step S403, the R1 reagent (R3 reagent) is aspirated by the R1 reagent dispensing arm 6 (R3 reagent dispensing arm 8). Thereafter, in step S404, the transmission output from the reader/writer substrate 17a to the antenna substrate 18b is set so that the antenna 18 (antenna) emits the long distance read electric wave and the long distance write electric wave in the range B (see FIG. 7) by the CPU 2a. In other words, the set value of the set value storing portion 17c of the reader/writer substrate 17a is set by the CPU 2a so that the read range and the write range of the antenna 18 become large. Thereafter, in step S405, the R1/R3 installing portion 161 is rotated in the direction of the arrow C1 or the direction of the arrow C2 so that the IC tag 22 of the R1 reagent container 19 of the write target is positioned at a position opposing the antenna 18 by the CPU 2a. In this case, the lid 19a of the R1 reagent container 19 (lid 20a of the R3 reagent container 20) is closed with the rotation of the R1/R3 installing portion 161.

In step S406, whether or not the R2 reagent container 21 is positioned in the region E (see FIG. 6) in the vicinity of the position opposing the antenna 18 is determined by the CPU 2a. In this case, whether or not the R2 reagent container 21 is positioned in the region E is determined based on the positional information of the R2 reagent container 21. Thus, if determined that the R2 reagent container 21 is positioned in the region E, in step S407, the R2 installing portion 162 is rotated in the direction of the arrow D1 or the direction of the arrow D2 so that the R2 reagent container 21 positioned in the region E is evacuated from the region E by the CPU 2a. The process then proceeds to step S412.

If determined that the reagent container of the aspirating target is the R2 reagent container 21 by the CPU 2a in step S401, the R2 installing portion 162 is rotated in the direction of the arrow D1 or the direction of the arrow D2 so that the R2 reagent container 21 of the aspirating target is positioned at the aspirating position at where the R2 reagent is aspirated by the R2 reagent dispensing arm 7 by the CPU 2a in step S408. In this case, the lid 21a of the R2 reagent container 21 is opened with the rotation of the R2 installing portion 162.

In step S409, the R2 reagent is aspirated by the R2 reagent dispensing arm 7. Thereafter, in step S410, the transmission output from the reader/writer substrate 17a to the antenna substrate 18b is set so that the antenna 18 emits the short distance read electric wave and the short distance write electric wave in the range A (see FIG. 6) by the CPU 2a. In other words, the set value of the set value storing portion 17c of the reader/writer substrate 17a is set by the CPU 2a so that the read range and the write range of the antenna 18 become small. Thereafter, in step S411, the R2 installing portion 162 is rotated in the direction of the arrow D1 or the direction of the arrow D2 so that the IC tag 23 of the R2 reagent container 21 of the write target is positioned at a position opposing the antenna 18 by the CPU 2a. In this case, the lid 21a of the R2 reagent container 21 is closed with the rotation of the R2 installing portion 162. The process then proceeds to step S412.

In step S412, the long distance read electric wave in the range B (short distance read electric wave in the range A) is emitted from the antenna 18 to the IC tag 22 (IC tag 23) of the write target by the CPU 2a. Thereafter, in step S413, whether or not the antenna 18 received the response electric wave within a predetermined time is determined by the CPU 2a. If determined that the antenna 18 did not receive the response electric wave within a predetermined time, the read error information is transmitted to the control device 4, and the notification that the write of the reagent information to the IC tag of the write target is not made is displayed on the display unit 4b of the control device 4 by the CPU 2a in step S414. The reagent aspirating/reagent information writing process is then terminated, and the process proceeds to step S5 shown in FIG. 14.

If determined that the antenna 18 received the response electric wave within a predetermined time in step S413, whether or not the reagent information contained in the response electric wave received by the antenna 18 is the reagent information recorded in the IC tag of the write target is determined by the CPU 2a in step S415. In this case, the CPU 2a determines whether or not the reagent information contained in the response electric wave is the reagent information recorded on the IC tag of the write target based on the reagent type (type specifying information) obtained from the response electric wave. If determined that the reagent information contained in the response electric wave is not the reagent information recorded on the IC tag of the write target, the process proceeds to step S414.

If determined that the reagent information contained in the response electric wave is the reagent information recorded on the IC tag of the write target, the long distance write electric wave or the short distance electric wave including the remaining amount information and the like of the reagent is transmitted from the antenna 18 to the IC tag 22 or IC tag 23 of the write target in step S416. In step S417, the information same as the reagent information written on the IC tag 22 or IC tag 23 of the write target is transmitted from the CPU 2*a* to the control device 4, and then the reagent aspirating/reagent information writing process is terminated, and the process proceeds to step S5 shown in FIG. 14. In the control device 4, the reagent information of the storage unit 4*d* is updated based on the reagent information transmitted from the CPU 2*a*.

In the present embodiment, the reagent information recorded in the IC tag 23 attached to the R2 reagent container 21 arranged in the R2 installing portion 162 and the reagent information recorded in the IC tag 22 attached to the R1 reagent container 19 arranged in the R1/R3 installing portion 161 are read by one antenna 18. The antenna 18 thus does not need to be individually arranged with respect to the R1/R3 installing portion 161 and the R2 installing portion 162 respectively, and the number of components can be suppressed from increasing by that much. Furthermore, only the region on the outer peripheral side of the R2 installing portion 162 needs to be ensured to arrange the antenna 18 and the region on the inner peripheral side of the R1/R3 installing portion 161 does not need to be ensured, and hence the region on the inner peripheral side of the R1/R3 installing portion 161 can be reduced. The main body of the immune analyzer 1 thus can be suppressed from becoming large.

In the present embodiment, the R2 reagent container 21 positioned in the region E is evacuated from the region E when the antenna 18 emits the long distance read electric wave in the range B. Therefore, the IC tag 22 of the R1 reagent container 19 can be suppressed from being difficult to read due to the positioning of the R2 reagent container 21 in the region E.

Furthermore, in the present embodiment, the gap F between the adjacent R2 reagent containers 21 and the IC tag 22 of the R1 reagent container 19 of the read target are arranged at the front surface position (opposing position) of the fixed antenna 18. Thus, the IC tag 22 and the antenna 18 can face each other at the front surface position of the antenna 18 through the gap F, and the IC tag 22 can be easily read by the antenna 18. Moreover, since the reading position of the antenna 18 can be fixed by fixing the antenna 18 at a predetermined position, the IC tag 22 and 23 can be easily read by the antenna 18.

In the present embodiment, the IC tag 23 of the R2 reagent container 21 is moved to a position not opposing the antenna 18 when the antenna 18 emits the long distance read electric wave in the range B. Thus, the IC tag 23 positioned at the position not facing the antenna 18 becomes hard to be read by the antenna 18, whereby the antenna 18 can be suppressed from mistakenly reading the IC tag 23 that is not the read target. The IC tag 22 of the R1 reagent container 19 of the read target can be more easily read by the antenna 18.

In the present embodiment, the read and write are carried out by the long distance read electric wave and the long distance write electric wave in the range B with respect to the IC tag 22 of the R1 reagent container 19 and the read and write are carried out by the short distance read electric wave and the short distance write electric wave in the range A smaller than the range B with respect to the IC tag 23 of the R2 reagent container 21. Thus, when reading the IC tag 23 of the read target, the antenna 18 is suppressed from mistakenly reading the IC tag 22 of the R1 reagent container 19 that is not the read target and the IC tag 23 of the peripheral R2 reagent container 21 adjacent to the R2 reagent container 21 attached with the IC tag 22 of the read target. Furthermore, the reagent information of the write target is suppressed from being written to the IC tag 22 of the R1 reagent container 19 that is not the write target and the IC tag 23 of the peripheral R2 reagent container 21 adjacent to the R2 reagent container 21 of the write target.

In the present embodiment, the read range of the antenna 18 can be limited to the range where only the IC tag 22 of the R1 reagent container 19 of the read target is positioned or the range where only the IC tag 23 of the R2 reagent container 21 is positioned by arranging the metal plate 18*e* for limiting the read range of the antenna 18. Thus, the antenna 18 is suppressed from mistakenly reading the IC tags 22 and 23 that are not the read target.

In the present embodiment, the antenna 18 is configured to be able to read the reagent information recorded in the IC tag 22 given to each of the twenty-five R1 reagent containers 19 and the reagent information recorded in the IC tag 23 given to each of the twenty-five R2 reagent containers 21 so as to receive the electric wave from a greater number of IC tags 22 and 23.

Furthermore, in the present embodiment, whether or not the reagent information contained in the response electric wave received by the antenna 18 is the reagent information of the read target is determined based on the reagent type (type specifying information) contained in the response electric wave by the CPU 2*a*. Thus, the response electric wave from the IC tags 22 and 23 that is not the read target can be suppressed from being mistakenly used as the response electric wave of the read target.

In the present embodiment, the reader/writer substrate 17*a* for acquiring the reagent information from the response electric wave emitted from the IC tags 22 and 23 in response to the read electric wave and the write electric wave and received by the antenna 18 is arranged. The reagent of the R1 reagent container 19, the reagent of the R3 reagent container 20, and the reagent of the R2 reagent container 21 can be individually managed based on the reagent information of the IC tags 22 and 23 acquired by the reader/writer substrate 17*a*.

In the present embodiment, when determined that the reagent information contained in the response electric wave is the reagent information of the read target, the long distance write electric wave (short distance write electric wave) including the reagent information to be updated is transmitted from the antenna 18 to the IC tag 22 (IC tag 23) of the write target. The CPU 2*a* thus can determine whether or not communicable with the IC tag 22 or 23 of the write target in advance before writing the reagent information to the IC tag 22 or 23 of the write target. The reagent information then can be more reliably written to the IC tags 22 and 23 of the write target.

The embodiments disclosed herein are illustrative and should not be construed as being restrictive in all aspects. The scope of the invention is defined by the scope of the claims rather than by the description of the embodiments, and meaning equivalent to the claims and all modifications within the scope is encompassed herein.

For instance, an example of applying the sample analyzer of the present invention to the immune analyzer 1 has been described in the embodiment, but the present invention is not limited thereto. The present invention can be applied to any apparatus including the antenna unit used to read the reagent information of the electronic tag, and is also applicable to a blood coagulation analyzer, a urine specimen measurement device, a gene amplification detection device and the like other than the immune analyzer.

An example in which the antenna 18 is arranged at the outer peripheral side of the R2 installing portion 162 has been described in the embodiment, but the present invention is not limited thereto. In the present invention, the antenna may be arranged at the inner peripheral side of the R1 installing portion. In this case, the device main body can be suppressed from becoming large as the region on the outer peripheral side of the R2 installing portion does not need to be ensured for the antenna.

In the above embodiment, an example of switching the read range of the read electric wave and the write range of the write electric wave emitted from the antenna 18 by switching the output of the reader/writer substrate 17a has been described, but the present invention is not limited thereto. For instance, the read range of the read electric wave and the write range of the write electric wave may be switched by configuring so that the shape and the size of the cutout of the metal plate (read limiting member) can be appropriately adjusted by the CPU.

An example in which the R1/R3 installing portion 161 and the R2 installing portion 162 are arranged in a substantially circular ring shape has been described in the embodiment, but the present invention is not limited thereto. For instance, the R1/R3 installing portion and the R2 installing portion may be arranged to extend linearly in a predetermined direction parallel to each other.

An example in which the antenna substrate 18b (antenna 18) is configured to be able to emit the read electric wave and the write electric wave has been described in the embodiment, but the present invention is not limited thereto. In the present invention, the antenna may be configured to emit only one of the read electric wave or the write electric wave.

An example in which the R1 reagent container 19 attached with the IC tag 22, the R2 reagent container 21 attached with the IC tag 23, and the R3 reagent container 20 not attached with the IC tag are arranged has been described in the embodiment, but the present invention is not limited thereto. In the present invention, only the reagent container attached with the IC tag may be arranged without including the reagent container not attached with the IC tag.

An example in which the reagent information of the R1 reagent of the R1 reagent container 19 and the reagent information of the R3 reagent of the R3 reagent container 20 held at the R1/R3 holding member 161a common with the R1 reagent container 19 are recorded in the IC tag 22 has been described in the embodiment, but the present invention is not limited thereto. In the present invention, three or more reagent information may be recorded on one IC tag.

An example in which twenty-five R1 reagent containers 19, twenty-five R3 reagent containers 20, and twenty-five R2 reagent containers 21 are arranged has been described in the embodiment, but the present invention is not limited thereto. In the present invention, the number of the R1 reagent container, the R3 reagent container, and the R2 reagent container may be differed. The number of R1 reagent container (R3 reagent container, R2 reagent container) may be other than twenty-five. For instance, only one of each of the R1 reagent container, the R3 reagent container, and the R2 reagent container may be arranged.

An example in which the R1/R3 installing portion 161 and the R2 installing portion 162 are respectively rotated by the inner side rotation drive portion 16d and the outer side rotation drive portion 16e has been described in the embodiment, but the present invention is not limited thereto.

In the present invention, the R1/R3 installing portion and the R2 installing portion may be configured so as not to rotate, and a drive portion for rotating the antenna may be arranged to rotate the antenna. In this case, the gap between the adjacent R2 reagent containers is preferably positioned in a region where the R1 reagent container of the R1/R3 installing portion and the antenna face each other.

In the embodiment, an example in which the R2 reagent container 21 positioned in the region E is evacuated from the region E when the antenna 18 emits the long distance read electric wave in the range B has been described, but the present invention is not limited thereto. In the present invention, the R2 reagent container positioned in the region E may not be evacuated from the region E as long as the antenna can read the IC tag of the R1 reagent container. For instance, the R2 reagent container may not be evacuated from the region E as long as the reagent remaining amount in the R2 reagent container becomes less and the electric wave from the antenna is not absorbed by the reagent of the R2 reagent container. The entire R2 reagent container may not be evacuated from the region E, and one part of the R2 reagent container may be positioned in the region E.

An example in which the gap F between the adjacent R2 reagent containers 21 and the IC tag 22 of the R1 reagent container 19 of the read target are arranged at the position opposing the antenna 18 has been described in the embodiment, but the present invention is not limited thereto. In the present invention, the gap F and the IC tag of the R1 reagent container of the read target may not be arranged at positions facing the antenna as long as the IC tag of the R1 reagent container can be read.

In the embodiment, an example in which the IC tag 23 of the R2 reagent container 21 is arranged at a position not facing the antenna 18 when the antenna 18 emits the long distance read electric wave in the range B has been described, but the present invention is not limited thereto. In the present invention, the IC tag of the R2 reagent container may be arranged at a position facing the antenna. In this case, only the reagent information of the IC tag of the R1 reagent container of the read target can be transmitted to the control device based on the reagent type (type specifying information) even when the IC tag of the R2 reagent container is read.

An example of performing read and write of the reagent information after the CPU 2a determines whether or not the R2 reagent container 21 is positioned in the region E in the vicinity of the position facing the antenna 18 has been described in the above embodiment, but the present invention is not limited thereto. In the present invention, the R2 installing portion may be moved to evacuate the R2 reagent container positioned in the region E from the region E only when the read and write of the reagent information is performed beforehand and the read and the write of the reagent information failed.

In the embodiment, an example in which the read and write are carried out by the long distance read electric wave and the long distance write electric wave in the range B with respect to the IC tag 22 of the R1 reagent container 19 and the read and write are carried out by the short distance read electric wave and the short distance write electric wave in the range A smaller than the range B with respect to the IC tag 23 of the R2 reagent container 21 has been described, but the present invention is not limited thereto. In the present invention, the read and write may be carried out by the read electric wave and the write electric wave in the same range with respect to the IC tag of the R1 reagent container and the IC tag of the R2 reagent container.

In the embodiment, the read (write) with respect to the IC tag 22 of the R1 reagent container 19 and the read (write) with respect to the IC tag 23 of the R2 reagent container 21 are separately carried out, but the read (write) with respect to the IC tag 22 and the read (write) with respect to the IC tag 23 may be simultaneously carried out in parallel.

What is claimed is:

1. A sample analyzer for analyzing a sample using a reagent in a reagent container comprising:
   a first reagent container holding unit configured to hold a first reagent container attached with a first electronic tag recorded with reagent information regarding a reagent;
   a second reagent container holding unit configured to hold a second reagent container attached with a second electronic tag recorded with reagent information regarding a reagent;
   a reagent information reading unit which comprises an antenna portion configured to emit an electric wave to the first electronic tag and the second electronic tag and to receive a response electric wave from the first electronic tag and the second electronic tag, and which reads the reagent information recorded in the first electronic tag and the reagent information recorded in the second electronic tag based on the response electric wave received by the antenna portion from the first electronic tag and the second electronic tag;
   a control unit configured to control the reagent information reading unit,
   a detector configured to measure a component contained in a measurement sample prepared from the sample and at least one of the first reagent and the second reagent; and
   a drive unit configured to move the first reagent container holding unit and the second reagent container holding unit,
   wherein the first reagent container holding unit holds a plurality of first reagent containers and is formed to a substantially circular shape in a plan view;
   wherein the second reagent container holding unit holds a plurality of second reagent containers and is formed to a substantially circular shape on an inner peripheral side of the first reagent container holding unit in the plan view,
   wherein the antenna portion is arranged on an outer peripheral side of the first reagent container holding unit,
   wherein the drive unit is configured to move the first reagent container holding unit to locate the first electronic tag of the first reagent container at a position facing the antenna portion when the first electronic tag is a read target,
   wherein the drive unit is configured to move the first reagent container holding unit to locate a gap between first reagent containers held adjacent to each other at a position facing the antenna portion and to move the second reagent container holding unit to locate the second electronic tag of the second reagent container at a position facing the antenna portion when the second electronic tag is the read target,
   wherein the control unit controls the reagent information reading unit to cause the antenna portion to emit an electric wave of a first reaching range to the first electronic tag, and to emit an electric wave of a second reaching range greater than the first reaching range to the second electronic tag, and
   wherein the antenna portion is attached to a housing of the first reagent holding unit.

2. The sample analyzer according to claim 1, wherein the antenna portion includes a shared antenna for selectively emitting the plurality of electric waves having mutually differing reaching ranges, and
   the control unit controls the reagent information reading unit to switch the electric wave emitted from the shared antenna in accordance with a read target being the first electronic tag or the second electronic tag.

3. The sample analyzer according to claim 2, further comprising a drive unit configured to move at least one of the first reagent container holding unit and the shared antenna,
   wherein the control unit controls the drive unit to evacuate the first reagent container from a position facing the shared antenna when the read target is the second electronic tag.

4. The sample analyzer according to claim 1, wherein the antenna portion includes a first antenna configured to emit the electric wave of the first reaching range and a second antenna configured to emit the electric wave of the second reaching range; and
   the control unit controls the reagent information reading unit to switch an antenna to emit the electric wave to the first antenna or to the second antenna in accordance with a read target being the first electronic tag or the second electronic tag.

5. The sample analyzer according to claim 1, wherein the control unit determines whether the reagent information is read from the electronic tag of a read target.

6. The sample analyzer according to claim 5, wherein the reagent information reading unit is configured to read, from each of the first electronic tag and the second electronic tag, a type specifying information for specifying a type of reagent; and
   the control unit determines whether the reagent information is read from the electronic tag of the read target based on the type specifying information read by the reagent information reading unit.

7. The sample analyzer according to claim 6, wherein the first reagent container holding unit is configured to hold the first reagent container which accommodates a reagent of a first type, and the second reagent container holding unit is configured to hold the second reagent container which accommodates a reagent of a second type that differs from the first type.

8. The sample analyzer according to claim 1, wherein the first reagent container holding unit is configured to hold a predetermined number of first reagent containers at equal respective intervals; and
   the second reagent container holding unit is configured to hold the predetermined number of second reagent containers at equal respective intervals.

9. The sample analyzer according to claim 1, wherein
   the second reagent container holding unit is configured to hold the second reagent container at a first position lateral to the first reagent container held by the first reagent container holding unit; and
   the antenna portion is arranged at a second position lateral to the first reagent container held by the first reagent container holding unit.

10. A sample analyzer for analyzing a sample using a reagent in a reagent container comprising:

a first reagent container holding unit configured to hold a first reagent container attached with a first electronic tag recorded with reagent information regarding a reagent;

a second reagent container holding unit configured to hold a second reagent container attached with a second electronic tag recorded with reagent information regarding a reagent;

a reagent information reading unit which comprises an antenna portion configured to emit a electric wave to the first electronic tag and the second electronic tag and to receive a response electric wave from the first electronic tag and the second electronic tag, and which reads the reagent information recorded in the first electronic tag and the reagent information recorded in the second electronic tag based on the response electric wave received by the antenna portion from the first electronic tag and the second electronic tag;

a control unit configured to control the reagent information reading unit, a detector configured to measure a component contained in a measurement sample prepared from the sample and at least one of the first reagent and the second reagent; and a drive unit configured to move the first reagent container holding unit and the second reagent container holding unit, wherein the first reagent container holding unit holds a plurality of first reagent containers and is formed to a substantially circular shape in plan view;

wherein the second reagent container holding unit holds a plurality of second reagent containers, and is formed to a substantially circular shape on an inner peripheral side of the first reagent container holding unit when seen in plan view;

wherein the antenna portion is arranged on an outer peripheral side of the first reagent container holding unit:

wherein the drive unit is configured to move the first reagent container holding unit to locate the first electronic tag of the first reagent container at a position facing the antenna portion when the read target is the first electronic tag;

wherein the drive unit is configured to move the first reagent container holding unit so as to locate a gap between the first reagent containers held adjacently each other at a position facing the antenna portion and to move the second reagent container holding unit so as to locate the second electronic tag of the second reagent container at a position facing the antenna portion when the read target is the second electronic tag, and wherein the antenna portion is attached to a housing of the first reagent holding unit.

11. The sample analyzer according to claim 10, wherein the antenna portion includes a first antenna configured to emit the electric wave of a first reaching range and a second antenna configured to emit the electric wave of a second reaching range; and the control unit controls the reagent information reading unit to switch an antenna to emit the electric wave to the first antenna or to the second antenna in accordance with a read target being the first electronic tag or the second electronic tag.

12. The sample analyzer according to claim 10, wherein the control unit determines whether the reagent information is read from the electronic tag of a read target.

13. The sample analyzer according to claim 12, wherein the reagent information reading unit is configured to read, from each of the first electronic tag and the second electronic tag, a type specifying information for specifying a type of reagent; and the control unit determines whether the reagent information is read from the electronic tag of the read target based on the type specifying information read by the reagent information reading unit.

14. The sample analyzer according to claim 13, wherein the first reagent container holding unit is configured to hold the first reagent container which accommodates a reagent of a first type, and the second reagent container holding unit is configured to hold the second reagent container which accommodates a reagent of a second type that differs from the first type.

15. The sample analyzer according to claim 10, wherein the first reagent container holding unit is configured to hold a predetermined number of first reagent containers at equal respective intervals; and the second reagent container holding unit is configured to hold the predetermined number of second reagent containers at equal respective intervals.

* * * * *